US005821350A

United States Patent [19]
Huang et al.

[11] Patent Number: 5,821,350
[45] Date of Patent: Oct. 13, 1998

[54] *ASPERGILLUS NIGER* BETA-GALACTOSIDASE GENE

[75] Inventors: Yue Huang, Vaudreuil; Costas N. Karatzas; Anthoula Lazaris-Karatzas, both of Beaconsfield; Annick Delaquis, St-Constant, all of Canada

[73] Assignee: Nexia Biotechnologies, Inc., Quebec, Canada

[21] Appl. No.: 551,459

[22] Filed: Nov. 1, 1995

[51] Int. Cl.$^6$ .................................................. C07H 21/04
[52] U.S. Cl. ........................................ 536/23.2; 536/23.7
[58] Field of Search .................................. 435/207, 320.1, 435/325, 354.3, 254.2, 252.3, 252.33; 536/23.2, 23.7

[56] References Cited

U.S. PATENT DOCUMENTS

| | | | |
|---|---|---|---|
| 3,629,073 | 12/1971 | Cayle | 195/62 |
| 3,919,049 | 11/1975 | Kiuchi et al. | 195/66 |

FOREIGN PATENT DOCUMENTS

| | | |
|---|---|---|
| 0574347A | 12/1993 | European Pat. Off. . |
| WO90/10703 | 9/1990 | WIPO . |
| WO94/23022 | 10/1994 | WIPO . |
| WO95/15390 | 6/1995 | WIPO . |
| WO95/17513 | 6/1995 | WIPO . |

OTHER PUBLICATIONS

Yamamoto, Yoshimi et al., DNA and Cell Biology, Isolation, Characterization, and Mapping of a Human Acid β–Galactosidase CDNA, vol. 9, No. 2, pp. 119–127 (1990).

Greenberg, N.A. et al., J. Food Sci., "Rapid Purification of β–Galactosidase (*Aspergillus niger*) from a Commercial Preparation", vol. 46, No. 3, pp. 684–687 (1981).

den Herder, I.F. et al. (1992) "Cloning and expression of a member of the *Aspergillus niger* gene family encoding alpha–galactosidase" Mol. Gen. Genet. 233:404–410.

Corazza et al., "62 –Galactosidase from *Aspergillus niger* in adult lactose malabsorption: a double–blind crossover study," *Aliment. Pharmacol. Therap.* 6:61–66 (1992).

Gouka et al., "A novel strategy for the isolation of defined pyrG mutants and the development of a site–specific integration system for *Aspergillus awamori*," *Curr. Genet.* 27:536–540 (1995).

Jacobson et al., "Three–dimensional structure of β–galactosidase from *E. coli*," *Nature* 369:761–765 (1994).

Jeenes et al., "A truncated glucoamylase gene fusion for heterologous protein secretion from *Aspergillus niger*," *FEMS Microbiology Letters* 107:267–272 (1993).

Kumar et al., "Saccharomyces Cerevisiae Cells Secreting an *Aspergillus Niger* β–Galactosidase Grow on Whey Permeate," *Bio/Technology* 10:82–85 (1992).

Nevalainen, "Induction, Isolation, and Characterization of *Aspergillus niger* Mutant Strains Producing Elevated Levels of β–Galactosidase," *Applied and Environmental Microbiology* 41:593–596 (1981).

Oakley et al., "Cloning, mapping and molecular analysis of the pyrG (orotidine 5'–phosphate decarboxylase) gene of *Aspergillus nidulans*," *Gene* 61:385–399 (1987).

(List continued on next page.)

*Primary Examiner*—Robert A. Wax
*Assistant Examiner*—Kawai Lau
*Attorney, Agent, or Firm*—Clark & Elbing LLP

[57] ABSTRACT

Disclosed are a cloned cDNA and a cloned genomic DNA, both encoding a β-galactosidase polypeptide from *Aspergillus niger*. Also disclosed are β-galactosidase expression vectors, transformed host cells that overexpress recombinant *A. niger* β-galactosidase, and *A. niger* host cell strains with disrupted endogenous β-galactosidase genes. Also disclosed are transgenic non-human mammals that express *A. niger* β-galactosidase.

3 Claims, 16 Drawing Sheets

OTHER PUBLICATIONS

Paige et al., "Lactose hydrolyzed milk," *Am. J. Clin. Nutrition* 28:818–822 (1975).

Poch et al., "Sequence of the Kluyveromyces lactis β-galactosidase: comparison with prokaryotic enzymes and secondary structure analysis," *Gene* 118:55–63 (1992).

Ramakrishnan et al., "Fermentation of Lactose by Yeast Cells Secreting Recombinant Fungal Lactase," *Applied and Environmental Microbiology* 59:4230–4235 (1993).

Rings et al., "Lactase: Origin, Gene Expression, Localization, and Function," *Nutrition Research* 14:775–797 (1994).

Rosado et al., "The Effect of the Digestion Products of Lactose (Glucose and Galactose) on Its Intra–intestinal, In Vivo . . . Beta–D–Galactosidase," *J. Am. College of Nutrition* 5:281–290 (1986).

Solomons et al., "Effective in vivo hydrolysis of milk lactose by beta–galactosidases in the presence of solid goods[1-3]," *Am J. of Clin. Nutrition* 41:222–227 (1985).

Ward et al., "A System for Production of Commercial Quantities of Human Lactoferrin: A Broad Spectrum Natural Antibiotic," *Bio/Technology* 13:498–502 (1995).

Widmer et al., "β–Galactosidase from *Aspergillus niger*," *Eur. J. Biochem* 100:559–567 (1979).

```
  1  CATCATGAAGCTTTCCTCCGCTTGTGCTATTGCCTTGCTGGCGGCACAGGCTGCTGGGGC
  1    M  K  L  S  S  A  C  A  I  A  L  L  A  A  Q  A  A  G  A

61  GTCCATTAAGCATCGAATCAATGGCTTTACCCTTACGGAGCATTCTGACCCGGCCAAGCG
 20   S  I  K  H  R  I  N  G  F  T  L  T  E  H  S  D  P  A  K  R

121  GGAACTGTTGCAGAAATACGTCACTTGGGATGACAAGTCCCTTTTTATCAATGGCGAAAG
 40    E  L  L  Q  K  Y  V  T  W  D  D  K  S  L  F  I  N  G  E  R

181  GATCATGATCTTCAGTGGGGAATTTCATCCATTCCGTCTACCTGTAAAAGAACTTCAGCT
 60    I  M  I  F  S  G  E  F  H  P  F  R  L  P  V  K  E  L  Q  L

241  TGACATCTTCCAGAAGGTCAAAGCTCTAGGGTTTAACTGTGTGTCTTTCTACGTCGATTG
 80    D  I  F  Q  K  V  K  A  L  G  F  N  C  V  S  F  Y  V  D  W

301  GGCCCCTCGTTGAAGGAAAAACCGGGGGAATACAGGGCAGACGGCATCTTTGATTTGGAGCC
100    A  L  V  E  G  K  P  G  E  Y  R  A  D  G  I  F  D  L  E  P

361  GTTCTTCGACGCGGCTTCGGAAGCAGGTATCTACCTGCTTGCCCGTCCAGGCCCGTACAT
120    F  F  D  A  A  S  E  A  G  I  Y  L  L  A  R  P  G  P  Y  I

421  CAACGCAGAGAGTTCCGGCGGTGGATTTCCGGGGTGGTTGCAGAGAGTCAATGGTACTCT
140    N  A  E  S  S  G  G  G  F  P  G  W  L  Q  R  V  N  G  T  L
```

Fig. 1

```
481  TCGCTCAAGCGGACAAGGCTTACCTGGATGCTACAGATAATTACGTCTCTCACGTCGCTGC
160   R   S   S   D   K   A   Y   L   D   A   T   D   N   Y   V   S   H   V   A   A

541  AACAATTGCCAAGTACCAGATTACCAATGGCGGTCCGATCATCCTGTATCAGCCCGAAAA
180   T   I   A   K   Y   Q   I   T   N   G   G   P   I   I   L   Y   Q   P   E   N

601  TGAGTACACTAGTGGCTGCTGCGGGTGTTGAATTCCCCGATCCCAGTGTACATGCAGTATGT
200   E   Y   T   S   G   C   C   G   V   E   F   P   D   P   V   Y   M   Q   Y   V

661  TGAAGACCAGGCTCGTAACGCCGGTGTCGTCATTCCATTGATCAATAACGATGCCTCGGC
220   E   D   Q   A   R   N   A   G   V   V   I   P   L   I   N   N   D   A   S   A

721  TTCCGGGAACAATGCTCCTGGAACCGGAGCAGTCGATATTTACGGCCATGATAG
240   S   G   N   N   A   P   G   T   G   K   G   A   V   D   I   Y   G   H   D   S

781  CTACCCGCTTGGGTTCGACTGCGCGAACCCTACGGGTATGGCCCTCGGGTGACCTACCTAC
260   Y   P   L   G   F   D   C   A   N   P   T   V   W   P   S   G   D   L   P   T

841  CAATTTCCGTACCCCTTCATCTTGAGCAAAGCCCGACCACACCATATGCGATAGTCGAGTT
280   N   F   R   T   L   H   L   E   Q   S   P   T   T   P   Y   A   I   V   E   F

901  CCAAGGCGGTTCGTACGACCCCTTGGGGAGGACCGGGATTCGCTGCGTGCTCCGAACTCCT
300   Q   G   G   S   Y   D   P   W   G   G   P   G   F   A   A   C   S   E   L   L
```

Fig. 1 cont.

```
 961  GAACAATGAGTTCGAGAGAGTGTTCTATAAGAACGACTTTAGCTTCCAGATTGCCATTAT
 320    N  N  E  F  E  R  V  F  Y  K  N  D  F  S  F  Q  I  A  I  M

1021  GAACCTCTACATGATCTTTGGTGGTGGAACTAACTGGGGTAACCTCGGTTATCCTAATGGATA
 340    N  L  Y  M  I  F  G  G  T  N  W  G  N  L  G  Y  P  N  G  Y

1081  CACCTCCTACGACTATGGTTCGGCTGTGACAGAATCTCGCAACATCACCCGCGAGAAATA
 360    T  S  Y  D  Y  G  S  A  V  T  E  S  R  N  I  T  R  E  K  Y

1141  CAGTGAACTCAAGCTACTTGCCAACTTTGCCAAAGTATCTCCGGGCTATTTGACGGCTAG
 380    S  E  L  K  L  L  G  N  F  A  K  V  S  P  G  Y  L  T  A  S

1201  TCCTGGCAATTTGACAACTTCCGGTTACGCTGATACCACAGACCTGACTGTAACGCCTTT
 400    P  G  N  L  T  T  S  G  Y  A  D  T  T  D  L  T  V  T  P  L

1261  GCTCGGAAACAGCACTGGCTCTTCTTCGTGGTCAGACATTCGGACTACAGCAGCGAAGA
 420    L  G  N  S  T  G  S  F  F  V  V  R  H  S  D  Y  S  S  E  E

1321  GTCAACATCATACAAGCTTCGTCTTCCTACCAGTGCCGGTAGCGTGACTATCCCTCAGCT
 440    S  T  S  Y  K  L  R  L  P  T  S  A  G  S  V  T  I  P  Q  L

1381  TGGTGGTACACTTCACACTTAATGGACGCCGATTCAAAGATACACGTGACCGACTACAATGT
 460    G  G  T  L  T  L  N  G  R  D  S  K  I  H  V  T  D  Y  N  V
```

Fig. 1 cont.

```
1441 CTCTGGAACCAATATATCATCTACTCCACGGCCGAGGTCTTTACCTGGAAGAAGTTCGCCGA
 480   S  G  T  N  I  I  Y  S  T  A  E  V  F  T  W  K  K  F  A  D

1501 CGGAAAGGTCCTCGTGCTCTACGGAGGTGCTGGTGAGCACCACGAACTTGCCATTTCAAC
 500   G  K  V  L  V  L  Y  G  G  A  G  E  H  H  E  L  A  I  S  T

1561 CAAGTCGAATGTCACGGTGATTGAAGGATCCGAGTCTGGCATCTCGTCAAAGCAGACCTC
 520   K  S  N  V  T  V  I  E  G  S  E  S  G  I  S  S  K  Q  T  S

1621 TTCGTCAGTTGTGGTCGGCTGGGATGTGTCGACCACTCGTCGTATCATCCAAGTTGGGGA
 540   S  S  V  V  V  G  W  D  V  S  T  T  R  R  I  I  Q  V  G  D

1681 CCTGAAAATTCTCCTTCTTGACAGGAACTCTGCCTATAACTACTGGGTGCCTCAACTTGC
 560   L  K  I  L  L  L  D  R  N  S  A  Y  N  Y  W  V  P  Q  L  A

1741 CACAGACGGCACTTCACCAGGTTTTAGCACCCCAGAGAAGGTCGCATCATCCATCATCGT
 580   T  D  G  T  S  P  G  F  S  T  P  E  K  V  A  S  S  I  I  V

1801 CAAAGCGGGCTACCTTGTTCGGACTGCTTACCTGAAGGGCAGCGGTCTTTACCTCACCGC
 600   K  A  G  Y  L  V  R  T  A  Y  L  K  G  S  G  L  Y  L  T  A

1861 AGACTTCAACGCTACCACTTCCGTTGAAGTCATTGGCGTCCCCTCCACTGCTAAGAATCT
 620   D  F  N  A  T  T  S  V  E  V  I  G  V  P  S  T  A  K  N  L
```

Fig. 1 cont.

```
1921 GTTCATCAATGGAGATAAGACATCGCACACCGTCGACAAGAACGGCATCTGGTCAGCTAC
 640  F  I  N  G  D  K  T  S  H  T  V  D  K  N  G  I  W  S  A  T

1981 AGTCGACTACAATGCCCCTGATATCTCGCTTCCCAGCCTGAAGGACTTGGACTGGAAGTA
 660  V  D  Y  N  A  P  D  I  S  L  P  S  L  K  D  L  D  W  K  Y

2041 CGTGGACACTCTTCCGGAGATCCAGTCCTCCTACGATGATTCTCTCTGGCCCGCCGCAGA
 680  V  D  T  L  P  E  I  Q  S  S  Y  D  D  S  L  W  P  A  A  D

2101 CCTCAAGCAGACCAAGAATACGCTTCGTTCTCTGACGACCCTACCTCTCTGTACTCATC
 700  L  K  Q  T  K  N  T  L  R  S  L  T  T  P  T  S  L  Y  S  S

2161 CGATTACGGCTTCCACACCGGATACCTGCTTTACCGCGGACACTTCACCGCCACGGGCAA
 720  D  Y  G  F  H  T  G  Y  L  L  Y  R  G  H  F  T  A  T  G  N

2221 CGAGAGCACCTTTGCTATCGATACGCAAGGTGGATCAGCATTTGGAAGCTCTGTCTGGCT
 740  E  S  T  F  A  I  D  T  Q  G  G  S  A  F  G  S  S  V  W  L

2281 GAACGGAACATACCTCGGTTCCTGGACTGGCCTTTATGCCAACTCCGACTACAATGCCAC
 760  N  G  T  Y  L  G  S  W  T  G  L  Y  A  N  S  D  Y  N  A  T

2341 TTACAATCTGCCTCAGCTCCAGGCAAGGCAAGACGTATGTGATCACCGTTGTGATCGACAA
 780  Y  N  L  P  Q  L  Q  A  G  K  T  Y  V  I  T  V  V  I  D  N
```

Fig. 1 cont.

```
2401 CATGGGCCTTGAGGAGAACTGGACTGTGTTGGTGAGGACCCTAATGAAGACCCCGCGTGGTAT
 800   M  G  L  E  E  N  W  T  V  V  G  E  D  L  M  K  T  P  R  G  I

2461 TCTCAACTTCCTGCTTGCCGGGACGGCCAAGCAGCGCAATTAGCTGGAAGTTGACCGGAAAA
 820   L  N  F  L  L  A  G  R  P  S  S  A  I  S  W  K  L  T  G  N

2521 CCTTGGCGGCGAGGACTACGAAGACAAGGTCCGAGGTCCTCTGAACGAGGGTGGTCTCTA
 840   L  G  G  E  D  Y  E  D  K  V  R  G  P  L  N  E  G  G  L  Y

2581 CGCTGAGCGCCGCCAAGGATTTCACCAGCCCGAGCCTCCCCAGCCAGAACTGGAAGTCTTCCAG
 860   A  E  R  Q  G  F  H  Q  P  E  P  P  S  Q  N  W  K  S  S

2641 CCCTCTGGAGGGTCTCTCTGAGGCAGGCATTGGTTTCTACAGCGCCAGTTTTGACCTTGA
 880   P  L  E  G  L  S  E  A  G  I  G  F  Y  S  A  S  F  D  L  D

2701 CCTGCCGAAGGGATGGGACGTGCCCCACTGTTCCTCAACATCGGTAACAGCACTACGCCATC
 900   L  P  K  G  W  D  V  P  L  F  L  N  I  G  N  S  T  T  P  S

2761 CCCGTACCGCGTGCAGGTCTACGTCAACGGATATCAGTATGCGAAATACATAAGCAACAT
 920   P  Y  R  V  Q  V  Y  V  N  G  Y  Q  Y  A  K  Y  I  S  N  I

2821 CGGACCTCAGACCTTCCCTGTCCCCGAGGAATCCTGAACTATCGCGGAACGAACTG
 940   G  P  Q  T  S  F  P  V  P  E  G  I  L  N  Y  R  G  T  N  W
```

Fig. 1 cont.

```
2881 GTTGGGCGGTGACCCTGTGGGCTCTCGACTCTCTGCCGGGCGGCAAGTTGGAAAGCTTGGAGTT
 960  L   A   V   T   L   W   A   L   D   S   A   G   G   K   L   E   S   L   E   L

2941 GAGTTACACCACTCCAGTGCTGACTGCCCTTGGGGAGGTCGAGTCGGTTGACCAGCCCAA
 980  S   Y   T   T   P   V   L   T   A   L   G   E   V   E   S   V   D   Q   P   K

3001 GTACAAGAAGCGGAAGGGTGCATACTAGGTTCTCTGTAAATAGCACATTCTATCTAGTT
1000  Y   K   K   R   K   G   A   Y  Stop
```

Fig. 1 cont.

```
   1  CATCATGAAG CTTTCCTCCG CTTGTGCTAT TGCCTTGCTG GCGGCACAGG CTGCTGGGGC
  61  GTCCATTAAG CATCGAATCA ATGGCTTTAC CCTTACGGAG CATTCTGACC CGGCCAAGCG
 121  GGAACTGTTG CAGAAATACG TATGTACGTC CATGGATGGA AGCACTTCTA GCAAACTGAC
 181  ATAGTGCCTA CTAGGTCACT TGGGATGACA AGTCCCTTTT TATCAATGGC GAAAGGATCA
 241  TGATCTTCAG TGGCGAATTT CATCCATTCC GGTACTACAG CCCTTCCTTC TTCTATCTAT
 301  ACTGAGGTGG ACTCGGGATT TTTTTGGAT TGCTCTAGTC TACCTGTAAA AGAACTTCAG
 361  CTTGACATCT TCCAGAAGGT CAAAGCTCTA GGGTTTAACT GTGTGTCTTT CTACGTCGAT
 421  TGGGCCCCTCG TTGAAGGAAA ACCGGGGGAA TACAGGGCAG ACGGCATCTT TGATTTGGAG
 481  CCGTTCTTCG ACGCGGCTTC GGAAGCAGGT ATCTACCTGC TTGCCCCGTCC AGGCCCGTAC
 541  ATCAACGCAG AGAGTTCCGG CGGTGGATTT CCGGGGTGGT TGCAGAGAGT CAATGGTACT
 601  CTTCGCTCAA GCGACAAGGC TTACCTGGAT GCTACAGATA AGTATGGTGA AACTCGCCCG
 661  GGAGGCCTAT GGCGCCTGCT GACTTTTCCA CAGTTACGTC TCTCACGTCG CTGCAACAAT
 721  TGCCAAGTAC CAGATTACCA ATGGCGGTCC GATCATCCTG TATCAGCCCG AAAATGAGTA
 781  CACTAGTGGC TGCTGCGGTG TTGAATTCCC CGATCCAGTG TACATGCCAG TATGTTGAAGA
 841  CCAGGCTCGT AACGCCGGTG TCGTCATTCC ATTGATCAAT AACGATGCCT CGGCTTCCGG
 901  GAACAATGCT CCTGGAACCG GGAAGGGAGC AGTCGATATT TACGGCCATG ATAGCTACCC
 961  GTAAGTTCAG CATGCCCTTG ACTGTGAACA CTGGCTGACA ATCATAGGCT TGGGTTCGAC
1021  TGCGTATGTT TATTCTTGAG TCTCGGTGTG CTTGTAGCTA ATTTGTCTAG GCGAACCCTA
1081  CGGTATGGCC CTCGGTGAC CTACCTACCA ATTTCCGTAC CCTTCATCTT GAGCAAAGCC
1141  CGACCACACC ATATGCGATA GTCGAGGTCA GTATATACGT ACTCTAGTCA GCATTGGGGG
1201  GCTAACACCT CGCAGTTCCA AGGCGGTTCG TACGACCCTT GGGGAGGACC GGGATTCGCT
1261  GCGTGCTCCG AACTCCTGAA CAATGAGTTC GAGAGAGTGT TCTATAAGAA CGACTTTAGC
```

Fig. 3

```
1321  TTCCAGATTG  CCATTATGAA  CCTCTACATG  GTACGTGCAT  GGATTTTTAC  GCTGGATTGC
1381  AGCTAATATG  TGTAGATCTT  TGGTGGAACT  AACTGGGGTA  ACCTCGGTTA  TCCTAATGGA
1441  TACACCTCCT  ACGACTATGG  TTCGGCTGTG  ACAGAATCTC  GCAACATCAC  CCGCGAGAAA
1501  TACAGTGAAC  TCAAGCTACT  TGGCAACTTT  GCCAAAGTAT  CTCCGGGCTA  TTTGACGGCT
1561  AGTCCTGGCA  ATTTGACAAC  TTCCGGTTAC  GCTGATACCA  CAGACCTGAC  TGTAACGCCT
1621  TTGCTCGGAA  ACAGCACTGG  CTCTTTCTTC  GTGGTCAGAC  ATTCGGACTA  CAGCAGCGAA
1681  GAGTCAACAT  CATACAAGCT  TCGTCTTCCT  ACCAGTGCCG  GTAGCGTGAC  TATCCCTCAG
1741  CTTGGTGGTA  CACTCACACT  TAATGGACGC  GATTCAAAGA  TACACGTGAC  CGACTACAAT
1801  GTCTCTGGAA  CCAATATCAT  CTACTCCACG  GCCGAGGTCT  TTACCTGGAA  GAAGTTCGCC
1861  GACGGAAAGG  TCCTCGTGCT  CTACGGAGGT  GCTGGTGAGC  ACCACGAACT  TGCCATTTCA
1921  ACCAAGTCGA  ATGTCACGGT  GATTGAAGGA  TCCGAGTCTG  GCATCTCGTC  AAAGCAGACC
1981  TCTTCGTCAG  TTGTGGTCGG  CTGGGATGTG  TCGACCACTC  GTCGTATCAT  CCAAGTTGGG
2041  GACCTGAAAA  TTCTCCTTCT  TGGTAGGTCC  ATCCAACTGT  CCGAGTTACA  TCAAGCTGAC
2101  TAGTATCAGA  CAGGAACTCT  GCCTATAACT  ACTGGGTGCC  TCAACTTGCC  ACAGACGGCA
2161  CTTCACCAGG  TTTTAGCACC  CCAGAGAAGG  TCGCATCATC  CATCATCGTC  AAAGCGGGCT
2221  ACCTTGTTCG  GACTGCGTAC  CTGAAGGGCA  GCGGTCTTTA  CCTCACCGCA  GACTTCAACG
2281  CTACCACTTC  CGTTGAAGTC  ATTGGCGTCC  CCTCCACTGC  TAAGAATCTG  TTCATCAATG
2341  GAGATAAGAC  ATCGCACACC  GTCGACAAGA  ACGGCATCTG  GTCAGCTACA  GTCGACTACA
2401  ATGCCCCTGA  TATCTCGCTT  CCCAGCCTGA  AGGACTTGGA  CTGGAAGTAC  GTGGACACTC
2461  TTCCGGAGAT  CCAGTCCTCC  TACGATGATT  CTCTCTGGCC  CGCCGCAGAC  CTCAAGCAGA
2521  CCAAGAATAC  GCTTCGTTCT  CTGACGACCC  CTGACTCTCT  CTACCTCTCC  GATTACGGCT
2581  TCCACACCGG  ATACCTGCTT  TACCGCGGAC  ACTTCACCGC  CACGGGCAAC  GAGAGCACCT
2641  TTGCTATCGA  TACGCAAGGT  GGATCAGCAT  TGGAAGCTC   TGTCTGGCTG  AACGGAACAT
2701  ACCTCCGGTTC CTGGACTGGC  CTTTATGCCA  ACTCCGACTA  CAATCCCACT  TACAATCTGC
```

Fig. 3 cont.

```
2761 CTCAGCTCCA GGCAGGCAAG ACGTATGTGA TCACCGTTGT GATCGACAAC ATGGGCCTTG
2821 AGGAGAACTG GACTGTTGGT GAGGACCTAA TGAAGACCCC GCGTGGTATT CTCAACTTCC
2881 TGCTTGCCGG ACGGCCAAGC AGCGCAATTA GCTGGAAGTT GACCGGAAAC CTTGGCGGCG
2941 AGGACTACGA AGACAAGGTC CGAGGTCCTC TGAACGAGGG TGGTCTCTAC GCTGAGCGCC
3001 AAGGATTTCA CCAGCCCGAG CCTCCCAGCC AGAACTGGAA GTCTTCCAGC CCTCTGGAGG
3061 GTCTCTCTGA GGCAGGCATT GGTTTCTACA GCGCCAGTTT TGACCTTGAC CTGCCGAAGG
3121 GATGGGATGT CCCACTGTTC CTCAACATCG GTAACAGCAC TACGCCATCC CCGTACCGCG
3181 TGCAGGTCTA CGTCAACGGA TATCAGTATG CGAAATACAT AAGCAACATC GGACCCTCAGA
3241 CCAGCTTCCC TGTCCCCGAG GGAATCCTGA ACTATCGCGG AACGAACTGG TTGGCGGTGA
3301 CCCTGTGGGC TCTCGACTCT GCCGGCGGCA AGTTGGAAAG CTTGGAGTTG AGTTACACCA
3361 CTCCAGTGCT GACTGCCCTT GGGGAGGTCG AGTCGGTTGA CCAGCCCAAG TACAAGAAGC
3421 GGAAGGGTGC ATACTAGGTT CTGTAAATAG CACATTCTAT CTAGTT
```

Fig. 3 cont.

ASPERGILLUS NIGER BETA-GALACTOSIDASE GENE

BACKGROUND OF THE INVENTION

This invention relates to lactose maldigestion, food processing, recombinant DNA technology, and enzymology.

Lactose is a disaccharide of glucose and galactose, which is found in milk at a concentration of approximately 46 g/liter. Lactose is cleaved into monosaccharides by the enzyme β-galactosidase (also known as lactase). β-galactosidase production is phylogenetically widespread (see, e.g., Poch et al., *Gene* 118:55–63 (1992)). β-galactosidases isolated from various organisms differ in properties such as molecular weight, glycosylation, pH optimum, thermostability, and whether or not they are secreted.

Most of the world's adult human population exhibits lactose maldigestion due to insufficient β-galactosidase in the mucosa of the small intestine. Symptoms of lactose maldigestion include nausea, flatulence, diarrhea or abdominal pain.

Food-grade β-galactosidase enzyme preparations from various microorganisms are commercially available. To reduce symptoms of lactose maldigestion, such preparations have been used to hydrolyze lactose in milk prior to consumption or taken in the form of a pill. See, e.g., Corazza et al., *Aliment. Pharmacol. Therap.* 6:61–66 (1992); Solomons et al., *Am. J. Clin. Nutr.* 41:222–227 (1985); Rosado et al., *J. Am. College Nutr.* 5:281–290 (1986); Paige et al., *Am. J. Clin. Nutr.* 28:818–822 (1975).

The pH optimum for the catalytic activity of β-galactosidase isolated from the filamentous fungus, *A. niger* is in the range of 2.5–4.0. This low pH optimum makes the *A. niger* enzyme suitable for processing acidified dairy products, e.g., acid whey and its permeate. This low pH optimum also makes *A. niger* β-galactosidase suitable for use in a gastric environment, e.g., the human stomach, to alleviate symptoms of lactose malabsorption. Another advantage of *A. niger* β-galactosidase is that it displays good thermostability and is useful at temperatures as high as about 60° C.

SUMMARY OF THE INVENTION

We have discovered an *A. niger* cDNA and an *A. niger* genomic DNA encoding a β-galactosidase polypeptide which differs substantially from the *A. niger* β-galactosidase polypeptide encoded by a known *A. niger* β-galactosidase cDNA.

In general, the invention features an isolated recombinant DNA molecule comprising a nucleotide sequence encoding an *A. niger* β-galactosidase polypeptide, which polypeptide includes an amino acid sequence substantially identical to (SEQ ID NO:1) or (SEQ ID NO:2).

In one embodiment of the invention, the isolated recombinant DNA molecule includes a cDNA sequence consisting of (SEQ ID NO:3). The invention also encompasses other nucleotide sequence encoding the polypeptide encoded by (SEQ ID NO:3), i.e., degenerate sequences. The invention also encompasses isolated recombinant DNA molecules that hybridize to a DNA molecule containing a sequence consisting of (SEQ ID NO:3) in a standard hybridization protocol under normal stringency conditions.

In another embodiment, the isolated recombinant DNA molecule includes a genomic DNA sequence encoding an *A. niger* β-galactosidase. In particular, the genomic DNA sequence can be (SEQ ID NO:5).

The invention also features a recombinant DNA vector that includes a nucleotide sequence encoding an *A. niger* β-galactosidase polypeptide, which polypeptide contains amino acid sequences substantially identical to (SEQ ID NO:1) and (SEQ ID NO:2). In one embodiment, the vector is a plasmid expression vector.

The invention also features a transformed host cell that has been transformed with a recombinant DNA vector encoding an *A. niger* β-galactosidase polypeptide, which polypeptide comprises amino acid sequences substantially identical to (SEQ ID NO:1) and (SEQ ID NO:2). The transformed host cell can be a eukaryotic cell, e.g., a fungal cell or a non-human mammalian cell. Alternatively, the transformed host cell can be a prokaryotic cell, e.g., an *E. coli* cell.

The invention also features a method for producing a recombinant *A. niger* β-galactosidase. The method includes the steps of: (a) isolating a recombinant DNA molecule comprising a nucleotide sequence encoding an *A. niger* β-galactosidase polypeptide, which polypeptide comprises amino acid sequences substantially identical to (SEQ ID NO:1) and (SEQ ID NO:2); (b) transforming a host cell with a DNA vector comprising a nucleotide sequence encoding an *A. niger* β-galactosidase polypeptide, which polypeptide comprises amino acid sequences substantially identical to (SEQ ID NO:1) and (SEQ ID NO:2), thereby producing a transformed host cell; (c) culturing said transformed host cell; and (d) recovering said *A. niger* β-galactosidase from said transformed host cell or from the growth medium surrounding said transformed host cell, thereby obtaining a recombinant *A. niger* β-galactosidase. This method can be used with a transformed host cell such as an Aspergillus cell or a yeast cell.

The invention also features a DNA targeting molecule capable of disrupting an endogenous β-galactosidase gene in an Aspergillus cell. The DNA targeting molecule can be used to produce an Aspergillus host cell that produces exclusively recombinant *A. niger* β-galactosidase.

As used herein, "disrupting sequence" means a nucleotide sequence located between flanking homologous sequences in a targeting molecule so as to prevent expression of a functional protein from a target gene, when the targeting molecule integrates at the target gene.

As used herein, "a functional protein" means a protein displaying biological activity, e.g., enzymatic activity.

As used herein, "homologous recombination" means the rearrangement of DNA segments at a sequence-specific site within or between DNA molecules through base pairing mechanisms.

As used herein, "isolated recombinant DNA" means DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA that is part of a hybrid gene encoding additional polypeptide sequence.

As used herein, "operably linked" means that a gene and a regulatory sequence(s) are connected in such a way as to permit gene expression when the appropriate molecules (e.g., transcriptional activator proteins) are bound to the regulatory sequence(s).

As used herein, "polypeptide" means any chain of amino acids, regardless of length or post-translational modification (e.g., glycosylation or phosphorylation).

As used herein, "standard hybridization protocol" means a protocol that includes hybridization using 6× SSC and 10–50% formamide at 22°–42° C., followed by washes using 0.1–2× SSC and 0.1–0.5% SDS at 22°–42° C.

As used herein, "substantially identical" means an amino acid sequence exhibiting at least 50%, preferably 85%, more preferably 90%, and most preferably 95% homology to a reference amino acid or nucleic acid sequence.

As used herein, "target gene" means a chromosomal gene in a living cell, which chromosomal gene is to be disrupted or replaced by a targeting molecule, by means of homologous recombination.

As used herein, "targeting molecule" means a linear or circular DNA molecule capable of specifically disrupting or replacing a target gene, by means of homologous recombination, upon transfection into a living cell containing the target gene.

As used herein, "transformed cell" means a cell into which (or into an ancestor of which) has been introduced, by means of recombinant DNA techniques, a DNA molecule encoding (as used herein) a β-galactosidase polypeptide.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present application, including definitions, will control. In addition, the materials, methods, and examples are illustrative only and not intended to be limiting.

Other features and advantages of the invention will be apparent from the following detailed description, and from the claims.

DETAILED DESCRIPTION

The drawings are first briefly described.

Drawings FIG. 1 is the nucleotide sequence of an *A. niger* cDNA encoding the β-galactosidase polypeptide of this invention. The deduced β-galactosidase amino acid sequence is indicated below the nucleotide sequence. Amino acid sequences which are unrelated to the amino acid sequences at corresponding regions of the *A. niger* β-galactosidase disclosed in PCT publication WO 90/10703 are shown by underlining.

FIG. 2 is a map of the *A. niger* β-galactosidase cDNA. The map shows differences between the coding sequence of the cDNA of the present invention and the coding sequence of the cDNA isolated from *A. niger* strain VTT-D-80144 and disclosed in PCT publication WO 90/10703. Letters beneath the cDNA indicate specific nucleotides that differ in the VTT-D-80144 sequence. A plus sign indicates an additional nucleotide in the VTT-D-80144 sequence. A minus sign indicates a nucleotide left out of the VTT-D-80144 sequence. No sign indicates a substitution, with the VTT-D-80144 nucleotide shown below. Dark areas are two cDNA segments encoding polypeptide domains with amino acid sequences essentially unrelated to any amino acid sequence encoded by the β-galactosidase cDNA in PCT publication WO 90/10703.

FIG. 3 is the nucleotide sequence of an *A. niger* genomic DNA encoding the β-galactosidase polypeptide of this invention.

Figure 2:
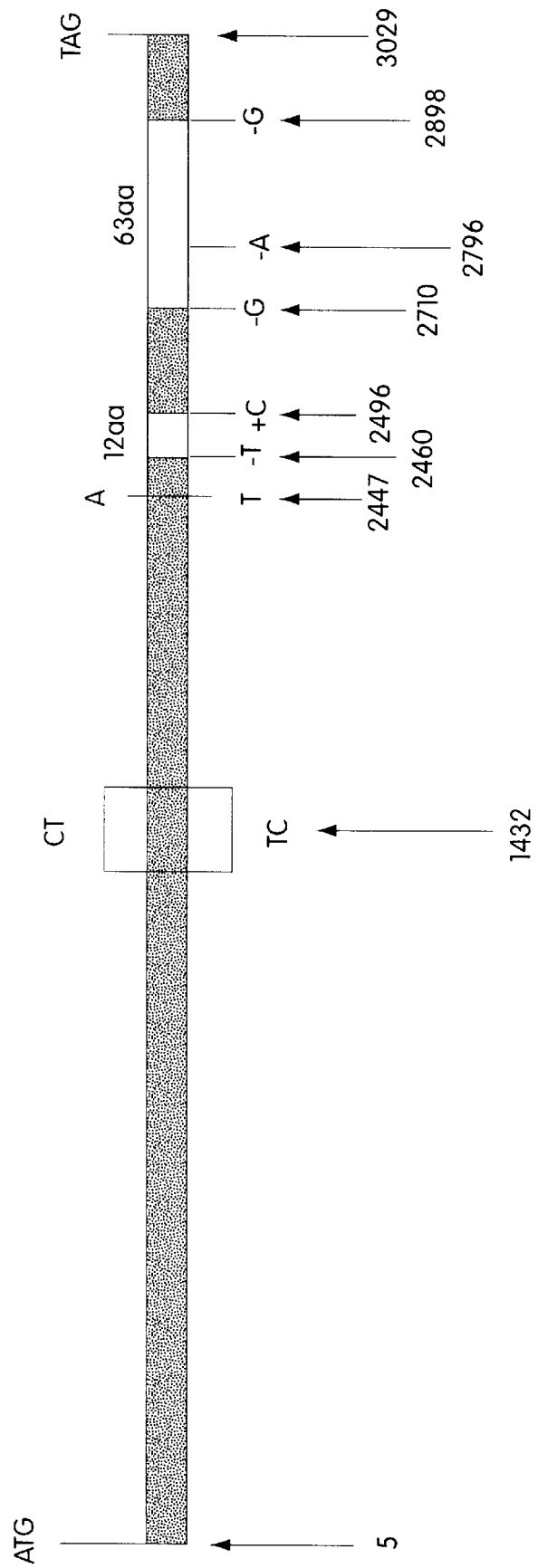

RECOMBINANT *A. niger* β-Galactosidase DNAs, EXPRESSION VECTORS AND HOST CELLS The present invention provides a cloned cDNA and a cloned genomic DNA, both encoding a β-galactosidase polypeptide from *Aspergillus niger*. The cloned *A. niger* β-galactosidase-encoding DNAs of this invention can be used for high level production of enzymatically active recombinant *A. niger* β-galactosidase.

The recombinant *A. niger* β-galactosidase produced using the DNA molecules, vectors, transformed host cells, and methods of this invention can be overexpressed in a transformed host cell, i.e., expressed at higher levels than the conventional non-recombinant enzyme is expressed in non-transformed cells.

The *A. niger* β-galactosidase produced according to this invention is synthesized as a precursor polypeptide comprising an amino-terminal signal peptide which causes the enzyme to be secreted from eukaryotic cells. Secretion facilitates high-level production of the enzyme in eukaryotic cells, because it allows biosynthesis to be sustained at rates that would quickly lead to cytotoxic intracellular accumulation of the enzyme, in the absence of secretion. In addition, secretion facilitates harvesting and purification of the β-galactosidase from the growth medium when the transformed host used for production of the enzyme is a eukaryote, e.g., *Aspergillus sp.* or yeast.

When the *A. niger* β-galactosidase-encoding sequences of this invention are used for production of a recombinant *A. niger* β-galactosidase, they are operably linked to suitable expression control sequences. The β-galactosidase-encoding sequences and operably linked expression control sequences are typically incorporated into an appropriate expression vector, which is used to transform an appropriate host cell.

Typically, an expression vector includes the following expression control sequences: a promotor, a transcription initiation start site, a ribosome binding site, and a transcription termination site. Additional expression control sequences can be included depending on considerations such as whether the host cell is prokaryotic or eukaryotic, and whether inducible expression of the β-galactosidase gene is desired. Expression control sequences suitable for various hosts are commercially available. Typically, commercially available expression control sequences are provided in compatible combinations incorporated into an essentially complete expression vector designed for use in a particular host, following insertion of the coding sequence to be expressed.

For the overexpression of the DNA sequence of this invention in an Aspergillus cell, the glucoamylase glaA promoter (Jeenes et al., *FEMS Microbiol. Let.* 107:267–272 (1993)) is preferred.

The expression vector comprising the *A. niger* β-galactosidase gene preferably comprises a selectable marker. The selectable marker provides for positive selection of host cells that have taken up the β-galactosidase expression vector in the host cell transformation procedure. Numerous selectable marker genes are known in the art, and many are commercially available. Essentially any selectable marker gene can be used in practicing this invention, as long as it is compatible with the host cell being transformed. When the host cell is *Aspergillus sp.*, a preferred selectable marker is the pyrG gene. When the host cell is a yeast, a preferred selectable marker gene is leucine-2. When the host cell is *E. coli*, a preferred selectable marker gene is a lactamase gene.

The expression vector can be an autonomously replicating vector, e.g., a plasmid. Alternatively, it can be a vector that integrates into the genome of the host cell. Vectors can be linear DNA molecules or closed circular DNA molecules.

Various host cell transformation procedures are known in the art. Examples of such transformation procedures include transfection of co-precipitates of calcium phosphate and DNA, DEAE-dextran mediated transfection, protoplast fusion, electroporation, lipid mediated techniques, and bombardment with high velocity micro projectiles. The selection and use of a suitable transformation procedure for a given vector/host-cell combination is within ordinary skill in the art.

Various host cells are useful for expressing DNA sequences of the present invention. The host cell can be prokaryotic or eukaryotic. Examples of useful prokaryotic host cells are *E.coli, Bacillus sp.*, and *Streptomyces sp.* Examples of useful eukaryotic host cells are animal cells, plant cells and fungal cells. For large scale production of *A. niger* β-galactosidase, fungal host cells are preferred, with Aspergillus cells and yeast cells being particularly preferred. For testing genetic constructs to be used for producing transgenic animals that express *A. niger* β-galactosidase, cultured mammalian cells are preferred host cells, with MAC-T cells (U.S. Pat. No. 5,227,301) being particularly preferred.

It will be recognized that not all vectors and expression control sequences will function equally well to express the DNA sequences of this invention. Neither will all hosts function equally well with a given expression vector system. For example, an autonomously replicating vector and host cell must be selected for compatibility, because the vector must be able to replicate in the host cell. The vector copy number, and the expression of any other genes on the vector (e.g., antibiotic resistance genes) should also be considered. Appropriate selection among the expression control sequences, vectors, and host cells, however, can be made by a person of ordinary skill in the art without undue experimentation and without departing from the scope of the invention.

The desired level of *A. niger* β-galactosidase expression can be obtained by varying factors such as the host cell type, the promotor used, the β-galactosidase copy number (in the host cell genome or per vector), vector copy number, level of inducer present (if an inducible promotor is used), and host cell culture conditions (e.g., nutrient availability, temperature, etc.).

Naturally occurring *A. niger* β-galactosidase is highly glycosylated. Where production of *A. niger* β-galactosidase in the glycosylated form is desired, the DNA of this invention is expressed in a transformed eukaryotic host cell.

When the invention is practiced using a eukaryotic host cell, it is preferable to use a genomic β-galactosidase DNA (i.e., one that includes introns) instead of a cDNA. When eukaryotic host cells are used for recombinant protein production, genomic sequences typically result in higher expression levels than comparable gene constructs in the same organism using a cDNA coding region (see, e.g., Palmiter et al., *Proc. Natl. Acad. Sci. USA* 88:478–482 (1991)). When the transformed host cell is a prokaryote, e.g., *E. coli*, a cDNA coding region must be used, because prokaryotic cells do not carry out mRNA splicing mechanisms.

Using the DNA molecules and the methods of this invention, recombinant *A. niger* β-galactosidase can be produced without glycosyl moieties. The present invention demonstrates that non-glycosylated *A. niger* β-galactosidase is enzymatically active.

Non-glycosylated β-galactosidase can be used in most situations where a glycosylated form of the enzyme can be used. In addition, there are some situations where the non-glycosylated form is preferred. For example, a non-glycosylated β-galactosidase is preferred for eliciting production of specific antibodies. The presence of the glycosyl moieties on β-galactosidase increases the likelihood that the elicited antibodies will cross-react with similar glycosyl moieties on proteins other than β-galactosidase. *A. niger* β-galactosidase-specific antibodies have various uses. For example, in research or quality control settings, they can be used to characterize (e.g., in standard Western blot procedures) or to quantitate (e.g., in standard ELISA procedures) β-galactosidase preparations.

When non-glycosylated β-galactosidase is desired, the DNA of this invention is expressed in a transformed prokaryotic host cell according to standard methods. A preferred prokaryotic host cell is *E. coli*. The use of *E. coli* cells as transformed host cells for production of recombinant proteins is known in the art. Expression vectors suitable for use in *E. coli* are commercially available.

The person of ordinary skill will recognize that the scope of the invention is not limited to the use of the vectors specifically exemplified herein. The design and construction of conventional expression vectors, or the modification of commercially available expression vectors, for expressing the DNA sequences of the present invention is within ordinary skill in the art. For a discussion of host cell transformation and expression of transgenes, see, e.g., Sambrook et al., *Molecular Cloning—A Laboratory Manual*, Cold Spring Harbor Press (1989); and Ausubel et al. (eds.) *Current Protocols in Molecular Biology*, John Wiley & Sons, Inc. (1994).

Disruption of *A. niger* Host Cell Endogenous β-Galactosidase Gene

When *A. niger* is used as a transformed host for selection or analysis of variant forms of β-galactosidase, the host cell's endogenous β-galactosidase gene is preferably disrupted or replaced. The confounding effects of the host cell's endogenous β-galactosidase are thereby advantageously avoided. Also, when *A. niger* is used as a transformed host for production of recombinant variant forms of β-galactosidase, the host cell's endogenous β-galactosidase gene is preferably disrupted or replaced. This simplifies purification protocols, by avoiding the need to isolate the desired variant form of β-galactosidase from the unwanted endogenous form. The disruption or replacement of endogenous β-galactosidase genes is typically accomplished by gene targeting, i.e., homologous recombination.

The first step in producing an *A. niger* host cell whose endogenous β-galactosidase genes have been disrupted or replaced is the preparation of a DNA targeting molecule. The targeting molecule is then transfected into the host cell, where it integrates into the host cell genome at the site of the endogenous β-galactosidase gene. Such DNA targeting molecules can be produced using information and processes known in the art.

Any DNA targeting molecule has two essential functions: (1) site-specific integration at the endogenous target gene, and (2) preventing expression of the endogenous target gene. These two essential functions depend on two basic structural features of the DNA targeting molecule. The first basic structural feature is a pair of flanking homologous sequences chosen to duplicate target gene sequences. The flanking homologous sequences cause the targeting molecule to undergo site-specific integration at the target gene, by base pairing mechanisms, i.e., by homologous recombination. Gene targeting, which affects the structure of a specific gene already in the host cell, is to be distinguished from other forms of stable transformation, wherein integration of foreign DNA for expression is not site-specific, and thus does not predictably affect the structure of any particular gene already in the cell.

The second basic structural feature of the targeting molecule is a disrupting sequence between the flanking homologous sequences. The disrupting sequence prevents expression of functional β-galactosidase protein from the endogenous β-galactosidase gene, following integration of the targeting molecule.

Numerous *A. niger* β-galactosidase gene targeting molecules can be constructed to fulfill the above structural and functional requirements. Parameters of the targeting molecule that can be varied include choice of the target gene sequences duplicated as the flanking homologous sequences of the targeting molecule, the lengths of the flanking homologous sequences, the length and identity of the disrupting sequence, and the portion of the target gene to be modified.

The lengths of the homologous sequences flanking the disrupting sequence of the targeting molecule can vary considerably. The flanking homologous sequences must be long enough for effective heteroduplex formation between one strand of the targeting molecule and one strand of the endogenous β-galactosidase gene. Increasing the length of the homologous sequences promotes heteroduplex formation and thus targeting efficiency. The incremental targeting efficiency accruing per additional homologous base pair diminishes, however, as the homologous sequences exceed several thousand base pairs. Preferably, the length of each flanking homologous sequence is between 50 and 5,000 base pairs. More preferably, the length of each flanking homologous sequence is between 300 and 1,500 base pairs. In practice, the precise length of the homologous regions in the DNA targeting molecule typically depends on the location of restriction sites in and around the endogenous β-galactosidase gene.

Any pair of endogenous β-galactosidase gene sequences can serve as flanking homologous sequences, as long as a critical portion of the endogenous β-galactosidase gene lies between the homologous sequences. A "critical portion" of the endogenous β-galactosidase gene is any portion of the gene without which functional β-galactosidase protein cannot be expressed. Preferably, no polypeptide is expressed from the endogenous β-galactosidase gene (as opposed to a non-functional polypeptide).

The flanking homologous sequences can be within the endogenous β-galactosidase coding region, but it is not necessary that they do so. For example, one flanking homologous region could be located 5' from the β-galactosidase gene and the other homologous region could be located within endogenous β-galactosidase coding region, or 3' to it. As a practical matter, other than the requirement that some critical portion of the endogenous β-galactosidase gene lie between the flanking homologous regions, the primary constraint on the choice of homologous sequences is the availability of the cloned sequences and the existence of restriction sites therein.

Preferably, the flanking homologous sequences do not include sequences longer than about 20 nucleotides that are known to occur elsewhere in the host cell genome. Excessive homology between the targeting molecule and non-target sites in the host cell genome can diminish targeting efficiency by diverting targeting molecules into non-productive heteroduplexes at non target sites.

It should be noted that homologous sequences in the target gene remain unchanged after integration of the targeting molecule. Those sequences are merely replaced by the duplicate (homologous) sequences in the targeting molecule.

The length of the disrupting sequence (between the flanking homologous regions) in the targeting molecule can also vary considerably. The minimum length of the disrupting sequence is one base pair. Insertion of a single base pair in the endogenous β-galactosidase coding sequence would cause a frame shift, which could prevent expression of a functional endogenous β-galactosidase protein, especially if the insertion is near the 5' end of the coding sequence. A single base pair change, however, is susceptible to reversion to the wild type sequence through spontaneous mutation. Therefore, disrupting sequences longer than one base pair are preferred. At the other extreme, an extremely long disrupting sequence is unlikely to confer any advantage over a disrupting sequence of moderate length, and it might diminish efficiency of transfection or targeting. A preferred length for the disrupting sequence is from 400 to 4,000 base pairs.

There is wide latitude in the choice of the disrupting sequence, because the disrupting function is not sequence specific. It is necessary, however, that the disrupting sequence does not express a protein or polypeptide toxic to the host cell.

The disrupting sequence can have a dual function, i.e., it can be both a selectable marker gene and a disrupting sequence. In that case, the length and identity of the disrupting sequence will be determined largely by the selectable marker gene and associated expression control sequences. The selectable marker gene provides for positive selection of transfected cells that have taken up a targeting molecule.

For producing an *Aspergillus sp.* host cell with a disrupted β-galactosidase gene, a preferred selectable marker/disrupting sequence comprises the pyrG (orotidine-5'-phosphate decarboxylase) gene of *A. nidulans* (Oakley et al., *Gene* 61:385–399 (1987).

β-Galactosidase Enzyme Assay and Purification

Recombinant *A. niger* β-galactosidase produced according to the present invention can be assayed for enzymatic activity using standard methods. A common industrial substrate for the enzyme, i.e., lactose, can be used to assay β-galactosidase activity. For example, since β-galactosidase hydrolyzes one lactose molecule to one glucose and one galactose molecule, the enzyme's activity can be assayed by measuring the release of galactose. In one such assay, galactose is oxidized by nicotinamide adenine dinucleotide ("NAD") to galactonic acid, in the presence of galactose dehydrogenase. The amount of resulting NADH is detected by its light absorbance at 334 nm.

Alternatively, a substrate analog can be used to assay β-galactosidase activity, according to standard methods. Substrate analogs typically release a colored product, or a fluorescent product, upon hydrolysis by β-galactosidase. Examples of chromogenic substrate analogs are 5-bromo-4-chloro-3-indoyl-D-galactopyranoside ("X-gal"), chlorophenol red-β-D-galactopyranoside ("CPRG"), and o-nitrophenyl-β-D-galactopyranoside ("ONPG"). An example of a substrate analog that releases a fluorescent product upon hydrolysis by β-galactosidase is 4-methylumbelliferyl-β-D-galactoside ("MUG") (Hubbes et al., Biochem. J. 285:827 (1992)).

Methods for purification of conventional (i.e., non-recombinant) β-galactosidase from Aspergillus are known in the art (see, e.g., Cayle U.S. Pat. No. 3,629,073; Kiuchi U.S. Pat. No. 3,919,049; and Widmer et al., Eur. J. Biochem. 100:559–567 (1979)). Such methods can be used to purify recombinant A. niger β-galactosidase produced according to the present invention.

In a preferred purification method, the recombinant A. niger β-galactosidase is collected from the transformed host cell growth medium, precipitated with 50% isopropanol (v/v), transferred to an aqueous buffer (pH approximately 5.7), and subjected to anion-exchange chromatography. A purity greater than 90% can be achieved using this series of steps. If higher purity is desired, additional purification steps can be employed, e.g., hydrophobic interaction chromatography or cation-exchange chromatography, or both (Widmer et al., supra).

Selection of A. niger β-Galactosidase Variants

The A. niger β-galactosidase sequences of this invention can be used for production and isolation of variant forms of A. niger β-galactosidase genes which encode novel β-galactosidase polypeptides with advantageous properties. Examples of such advantageous properties are increased enzyme turnover rate, lower pH optimum, insensitivity to galactose (i.e., reduced end-product inhibition), and cold sensitivity (e.g., inactive at 4° C./active at 37° C.).

The template for mutagenesis can be the whole gene, or it can be a specific region of the gene. Mutagenesis could be random or it could be site-directed. Standard PCR methods can be used for mutagenesis (see, e.g., Fromant et al., Anal. Biochem. 224:347–353 (1995); Lehtovaara et al., Protein Engineering 2:63–68 (1988); Cadwell et al., PCR Methods and Applications 2:28–33 (1992); and Gatlin et al., Biotechniques 19:559–564 (1995).)

Alternatively, chemical mutagenesis can be carried out according to standard procedures. Preferred chemical mutagenesis agents include methoxylamine hydrochloride (see, e.g., Kadonaga et al., Nucleic Acids Res. 13:1733–1745 (1985); Adams et al., J. Biol. Chem. 269:5666–5672 (1994)); nitrous acid, formic acid, hydrazine and potassium permanganate (see, e.g., Milton et al., J. Biol. Chem. 261:16604–16615 (1986)). A host organism harboring a transfected A. niger β-galactosidase can be mutated by UV or chemical methods. The mutagenized cells can be subjected to a screening process, e.g., for growth on lactose media.

The mutated A. niger β-galactosidase genes, or gene fragments, are ligated into an appropriate expression vector. The expression vector is then used to transform prokaryotic or eukaryotic cells. The transformed cells are subjected to a suitable selection (screening) protocol designed to identify clones exhibiting the desired characteristic. For example, a transformed cell containing a gene encoding a cold sensitive form of A. niger β-galactosidase can be identified in a selection protocol essentially as described by Adams et al. (supra). In another example, transformants are replica-plated on an indicator medium containing sufficient galactose to inhibit the activity of the template β-galactosidase, but not the activity of selected variants.

Production of Transgenic Animals Expressing A. niger β-galactosidase

Secreted A. niger β-galactosidase can be expressed in the secretory cells of the mammary gland of a non-human mammal. Preferably, the non-human mammal is bovine.

In such a transgenic non-human mammal, lactose is synthesized and secreted normally into the mammal's milk. The lactose is hydrolyzed, however, by recombinant A. niger β-galactosidase, which is secreted into the mammal's milk. Therefore, milk from the transgenic non-human mammal contains a reduced lactose content.

Preferably, the A. niger β-galactosidase expression is mammary gland-specific. Mammary gland specific expression can be obtained by operably linking the A. niger β-galactosidase-encoding cDNA or genomic DNA to mammary gland-specific expression control sequences, e.g., expression control sequences from genes encoding casein (αS1, αS2, β, or κ) or whey proteins (α-albumin or β-albumin) or lactoferrin. Secretion of the β-galactosidase polypeptide can be directed by the signal peptide of the A. niger β-galactosidase or by a signal peptide of a milk protein gene, e.g., casein.

Transgenic animals are produced by standard methods, e.g., microinjection of the expression vector intopronuclei of fertilized oocytes, or transfection of embryonic stems cells. See, e.g., Krimpenfort et al., Bio/Technology 9:844–847 (1991).

Preferably, a recombinant A. niger β-galactosidase gene construct is tested in a cultured cell line before being used for production of a transgenic non-human mammal. A cultured cell line preferred for testing the genetic constructs of this invention is a bovine mammary epithelial cell line designated MAC-T and described in U.S. Pat. No. 5,227, 301.

MAC-T cells display several features of differentiated mammary epithelia. For example, these cells feature apical microvilli and apical junctional complexes, imparting on the cells an apical-basal polarity. In addition, they form high resistance monolayers. In the presence of extracellular matrix and lactogenic hormones, MAC-T cells differentiate and secrete endogenous, mammary-specific proteins. If desired, MAC-T cells can be used for testing genetic constructs to be introduced into any ruminant, including constructs to be introduced into sheep and goats. Thus, these cells provide an art-recognized model system for ruminant mammary glands.

MAC-T cells can be cultivated on tissue culture plastic in standard cell culture media. For example, complete media composed of Dulbecco's Modified Eagle's medium (DMEM) supplemented with 10% fetal bovine serum (FBS), 5 μg/ml insulin, 1 μg/ml hydrocortisone, 1–5 μg/ml prolactin, and 50 μg/ml gentamycin incubated in 5% carbon dioxide, water-saturated atmosphere at 37° C. provides suitable growth conditions for the cell line (Huynh et al., 1991, Exp. Cell Res. 197:191–199). One day prior to transfection, the MAC-T cells can be treated with trypsin and plated at the desired density; a density of 1 to $1.5 \times 10^5$ cells/35 mm dish is suitable. Approximately 48 hours after transfection, a sample of the cell culture medium is collected and assayed for the presence of the recombinant proteins.

Experimental Information

Growth of A. niger Mycelia

Messenger RNA and genomic DNA were isolated from A. niger strain A733 (Fungal Genetics Center, Kansas City, Kans.).

One liter of complete growth media (CM) for A. niger was composed of 50 ml of 20× Salt Mix (per liter: 120 g $NaNO_3$, 10.4 g KCl, 16.3 g $KH_2PO_4$, 20.9 g $K_2HPO_4$), 1.0 ml Hunter's Trace Element (per liter: 22.0 g $ZnSO_4*7H_2O$, 1.1 g $(NH_4)_6Mo_7O_{24}*4H_2O$, 11.0 g $H_3BO_3$, 5.0 g $MnCl_2*4H_2O$, 5.0 g $FeSO_4*7H_2O$, 1.6 g $CoCl_2*6H_2O$, 1.6 g $CuSO_4*5H_2O$, EDTA 72 g), 5 ml of 2.25M $MgSO_4$, 2.0 g bactopeptone, 1.0 g yeast extract, 1.0 g Casamino acids, 10.0 g glucose, and vitamin supplements. Conidia were inoculated into complete media for $10^6$/ml and incubated in 30° C. for 24 hours. Mycelia were harvested and frozen immediately and stored at −70° C.

Cloning and Analysis of cDNA Encoding A. niger β-Galactosidase

The starting material for the isolation of mRNA was 0.3 g of frozen mycelia (strain A733). The mRNA isolation was carried out using a commercial kit, essentially according to the vendor's instructions (Quickprep Micro mRNA Purification Kit™, Pharmacia LKB, Piscataway, N.J., cat. no. 27-9255-01). The cDNA first strand was synthesized from purified mRNA using the First-Strand cDNA Synthesis Kit (Pharmacia cat. no. 27-9261-01).

The β-galactosidase gene was amplified from the first strand cDNA mixture using polymerase chain reaction ("PCR"). PCR primers were designed according to the published cDNA sequence of A. niger mutant VTT-D-80144 strain β-galactosidase gene (WO 90/10703). The 5' primer for PCR consisted of the following sequence:

5' ATTAGAGCTC ATGAAGCTTT CCTCCGCTTG TG 3' (SEQ ID NO:6). The 3' primer for PCR consisted of the following sequence:

5' ATTAAGATCT CGAGAATGTG CTATTTACAG AACCTA 3' (SEQ ID NO:7). PCR amplification was performed in a 100 μl reaction containing 33 μl of first strand cDNA mixture, 2.5 units of Taq DNA polymerase (Promega, Madison, Wis.), 0.2 mM of each deoxyribonucleotide (dNTP), 0.25 uM of each primer and the thermo DNA polymerase buffer. The reaction was carried out in MiniCycler™ (MJ Research Inc., Watertown, Mass.) using the following program: denaturation at 94° C. for 3 minutes; 30 cycles each consisting of 1 minute at 94° C., 1 minute at 60° C., 3 minutes at 72° C.; and a final extension step of 7 minutes at 72° C. The PCR product was identified on 0.8% agarose gel as a 3 kb band. This band was purified using QIAEX Gel Extraction Kits (Qiagen Inc, Chatsworth, Calif., cat. no. 20020). The purified DNA fragment was digested by restriction endonucleases SacI and BglII, and was cloned into pSP72 (Promega cat. no. P2191) vector to generate plasmid pNB4.

The entire coding region of β-galactosidase cDNA was sequenced using an automated sequencing system and standard methods. FIG. 1 shows the nucleotide sequence of a cDNA encoding the full-length A. niger β-galactosidase and the deduced amino acid sequence. An open reading frame ("ORF") was found from position 4 to 3029. The ORF encoded a polypeptide of 1007 amino acids, with a calculated molecular weight of 109.6 kD. Computer analysis of the N-terminal sequence of the polypeptide showed the presence of a signal peptide which could direct protein secretion. The first 19 amino acids of the polypeptide formed a hydrophobic core, a basic residue (lysine) after start codon (Met) at the N-terminal, and a putative signal sequence cleavage site at its C-terminal.

A putative KEX2 cleavage site (Innis et al., Science 228:21–26 (1985)) (KR) was identified at position 39. Microsequencing confirmed that the mature/secreted β-galactosidase polypeptide starts with amino acid residue number 40. The mature polypeptide contains 968 amino acid residues and has a predicted molecular weight of 106 kD.

We have identified 13 putative N-linked glycosylation sites within the mature β-galactosidase amino acid sequence. This is consistent with the high level of glycosylation (10–30%) previously reported for the A. niger β-galactosidase. When a partially purified preparation of A. niger β-galactosidase was treated with endo-H (deglycosylates N-linked sugars), the estimated protein molecular weight (by SDS-PAGE) decreased from approximately 150 kD to approximately 110 kD, indicating a high degree of N-linked sugars.

The A. niger β-galactosidase polypeptide encoded by the cDNA of the present invention was found to be significantly different from the β-galactosidase polypeptide encoded by a cDNA ("cDNA-K") from A. niger strain VTT-D-80144 (WO 90/10703). The A. niger cDNA of the present invention encodes a polypeptide of 1007 amino acids. The cDNA of Hartley et al. (WO 90/10703) encodes a polypeptide of 1006 amino acid residues. FIG. 2 is a schematic diagram illustrating the differences between the A. niger β-galactosidase cDNA sequences of the present invention and the β-galactosidase cDNA sequence known from A. niger strain VTT-D-80144. Compared to the present cDNA, cDNA-K lacks a "T" at position 2460 and contains an extra "C" at position 2496. This results in a frame shift which changes 12 contiguous amino acids. cDNA-K lacks also a "G" at position 2710, an "A" at position 2796 and a "G" at position 2898. This results in frame shift which changes 63 contiguous amino acids. Thus, two regions of the protein encoded by the DNA of the present invention are completely different from any region found in the β-galactosidase of A. niger strain VTT-D-80144.

Cloning and Analysis of Genomic DNA Encoding A. niger β-Galactosidase

The starting material used for isolation of an A. niger genomic β-galactosidase gene was 0.3 grams of frozen mycelia (strain A733). The mycelia were homogenized in 200 μl of TE buffer (10 mM Tris-HCl, pH 8.0, 1 mM EDTA) and 1% SDS using a glass homogenizer. The mixture was transferred to a microcentrifuge tube and 400 μl of Solution II (0.2N NaOH, 1% SDS) was added. After vortexing for 5 minutes, 300 μl of Solution III (3M sodium acetate, pH 5) was added to precipitate the broken cells. DNA was recovered by precipitating it with an equal volume of isopropanol. The DNA was resuspended in 200 μl TE buffer containing 50 μg/ml of RNAse A (Pharmacia, cat. no. 27-0323-01).

The genomic β-galactosidase gene of A. niger was amplified by standard PCR methods. The PCR primers were the same as those used for amplification of the A. niger β-galactosidase cDNA (described above). PCR amplification was performed in a 100 μl reaction containing 1 μl of A. niger genomic DNA, 2.5 units of Taq DNA polymerase (Promega, Madison, Wis.), 0.2 mM of each dNTP, 0.25 μM of each primer and thermo DNA polymerase buffer. The reaction was carried out in a MiniCycler™ using the following program: denaturation at 94° C. for 3 min; 30 cycles each consisting of 1 min at 94° C., 1 min at 60° C., 4 min at 72° C.; and a final extension step of 7 minutes at 72° C. The PCR product was identified on a 0.8% agarose gel as a 3.5 kb band, and further purified using Wizard DNA Cleanup System™ (Promega, Madison, Wis., cat. no. A7280). Purified DNA was digested by restriction endonucleases SacI and BglII. It was then cloned into the pSP72 vector to generate plasmid pNB5.

Figure 4:
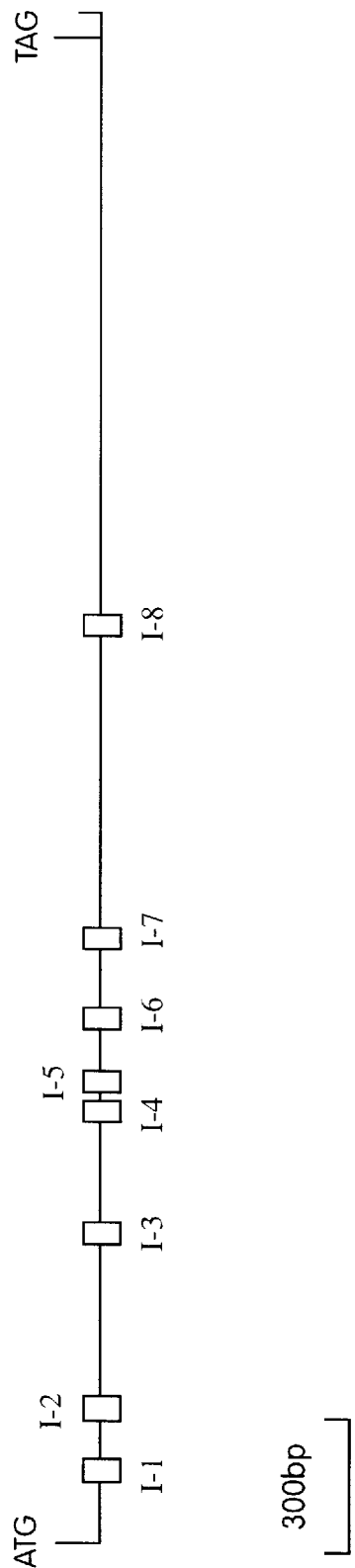
FIG. 4 is a map showing the structure of the *A. niger* β-galactosidase genomic DNA of this invention. The genomic DNA contains eight introns whose locations are indicated by rectangles labeled I-1 to I-8.

The entire coding region (with introns) of genomic β-galactosidase gene was sequenced using an automated sequencing system and standard methods. FIG. 3 shows the sequence of genomic clone of A. niger β-galactosidase gene. FIG. 4 is a schematic representation of the genomic gene structure.

Eight introns were found in the genomic β-galactosidase gene by comparison to the cDNA sequence. All introns contained putative intron splicing sites similar to those found in higher eukaryotes, and they were relatively small and similar in size. The largest intron (I-2) is 66 base pairs and the smallest one (I-7) is 45 base pairs.

Overexpression of Recombinant A. Niger β-galactosidase in Aspergillus niger

Figure 6:
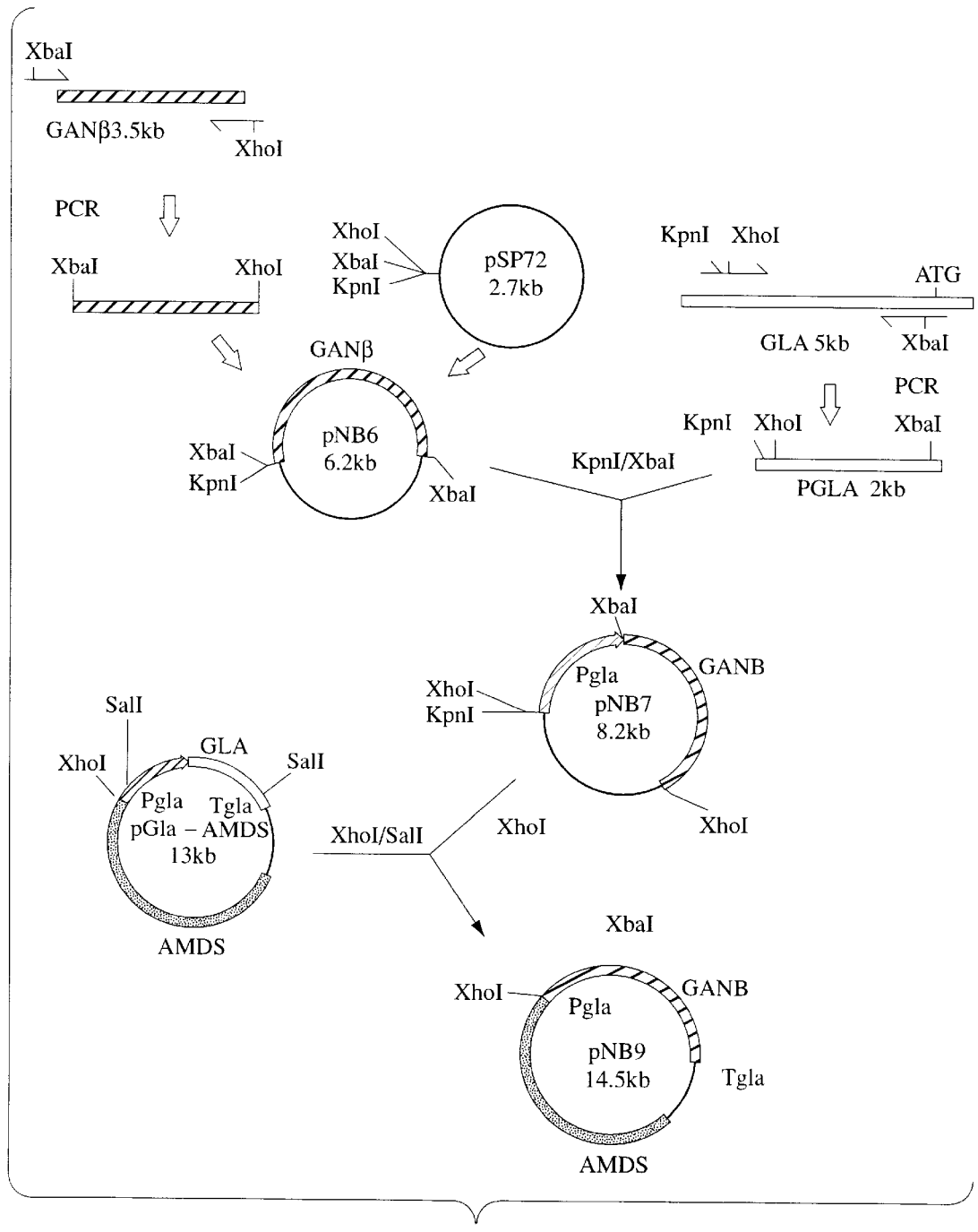
FIG. 6 is a schematic diagram showing the cloning strategy for the construction of *A. niger* β-galactosidase *A. niger* expression vector pNB9.

Plasmid pGLA-AMDS was used to construct expression vectors. Plasmid pGLA-AMDS contained a pUC19 backbone, the acetamidase gene ("AMDS gene") of Aspergillus nidulans (Corrick et al., Gene 53:63–71 (1987)) as the selectable marker, the A. niger glucoamylase promoter (Fowler et al., Curr. Genet. 18:537–545 (1990)), and its coding region. The expression vector, pNB9, was constructed by replacing the coding region of glucoamylase gene with the genomic gene of β-galactosidase of A. niger. FIG. 6 illustrates the construction of pNB9.

PCR cloning was used to place the A. niger β-galactosidase gene under the control of the glucoamylase promoter. The entire β-galactosidase genomic gene coding region was amplified by PCR.

The nucleotide sequence of the 5'-end PCR primer consisted of: 5' GAGTCTAGAT ACAATGAAGC TTTCCTCCGC TTGTG 3' (SEQ ID NO:8). The nucleotide sequence of the 3'-end PCR primer consisted of: 5' ATTAAGATCT CGAGAATGTG CTATTTACAG AACCTA3' (SEQ ID NO:9). These primers were used to amplify the genomic β-galactosidase gene, so an XbaI site was introduced at the 5'-end, and an XhoI site at the 3'-end.

The PCR product was cloned into the vector pSP72, to generate an intermediate vector designated pNB6. A 2-kb DNA fragment of the glucoamylase promoter was amplified by PCR. Using the 5'-end PCR primer 5' TTAGGTACCT CGAGGATTGT CTGAACATT 3' (SEQ ID NO:10) and 3'-end PCR primer 5' GCGTCTAGAG GTGTAATGAT GCTGGGGA3' (SEQ ID NO:11), a KpnI site was introduced to the 5'-end of the promoter DNA fragment and an XbaI site at the 3'-end. The PCR product containing glucoamylase promoter was then cloned into plasmid pNB6, in front of the β-galactosidase gene coding region, to generate plasmid pNB7. Finally, pNB7 was digested by XhoI, a 5-kb fragment containing the glucoamylase promoter and β-galactosidase gene was purified and cloned into the vector pGLA-AMDS, to generate plasmid pNB9.

An A. niger strain (A920; cspA; fwnA1; pyrA5; nicb5) was co-transformed with plasmid pNB9 and plasmid pPyrG using the protocol described above. Seventy-five transformants were obtained and assayed for β-galactosidase activity. All the transformants were inoculated in 5 ml of liquid cultures containing minimum medium and selection and incubated for 2, 4, and 7 days at 30° C. with shaking at 200 rpm.

The secreted β-galactosidase activity was monitored by the ONPG activity of the cultures. Eight clones were identified as high producers of β-galactosidase. These clones were used for further studies by Western blotting, deglycosylation, microsequencing, and Southern blotting.

Vector for Expression of Recombinant A. niger β-Galactosidase in Yeast

Figure 7:
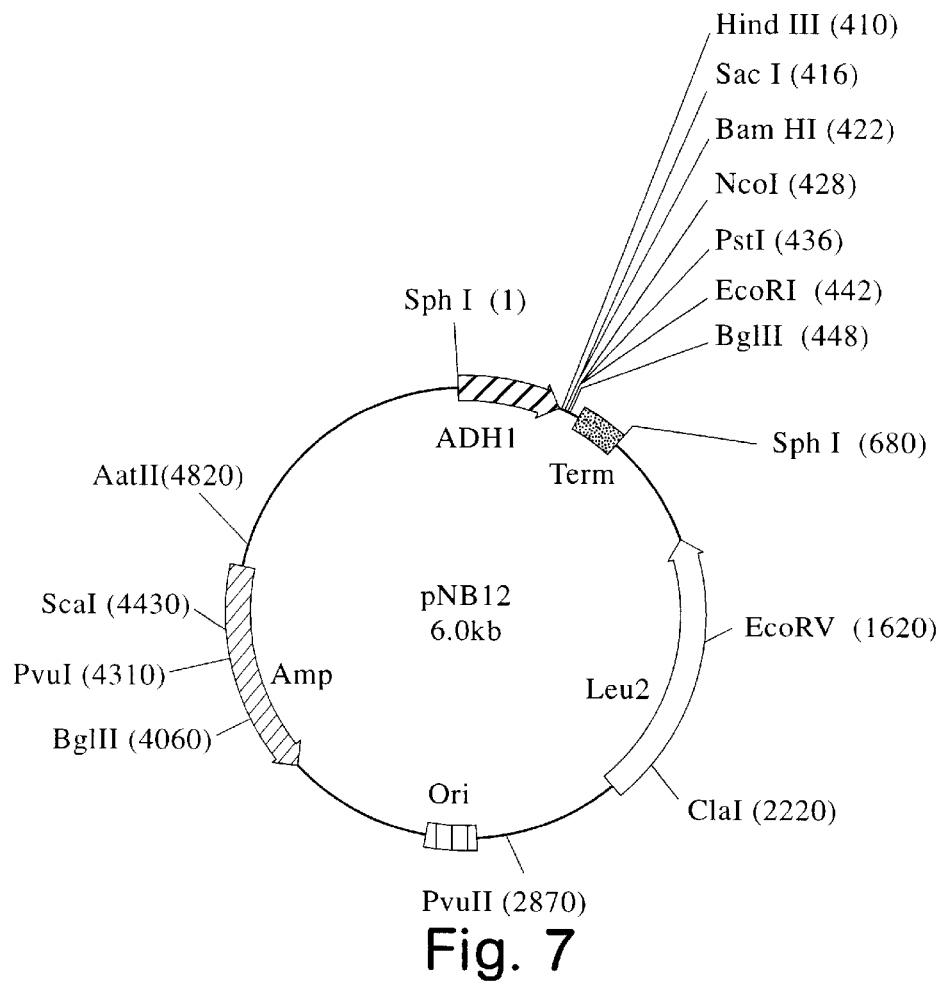
FIG. 7 is a restriction map of *A. niger* β-galactosidase yeast expression vector pNB12.

The yeast activation domain vector pGAD424 (ClonTech, Palo Alto, Calif., cat. no. K1605-B) was modified for expression of A. niger β-galactosidase DNA fragment. Plasmid pGAD424 was digested by HindIII to remove a 705 base pair fragment. The digestion product was treated with calf intestine phosphatase (Boehringer Mannheim, Indianapolis, Ind., cat. no. 836311), then ligated to a linker DNA sequence containing the following multiple cloning sites: HindIII, SacI, BamHI, NcoI, PstI, EcoRI and BglII. The resulting plasmid, pNB12, was suitable for insertion of the A. niger β-galactosidase gene as a 3 kb SacI-BlgII fragment. FIG. 7 shows the restriction map of vector pNB12.

Plasmid pNB5 carrying the β-galactosidase cDNA was digested by restriction enzymes SacI and BglII. The 3 kb fragment containing cDNA β-galactosidase gene was purified and then ligated to vector previously cut by the same restriction enzymes. The resulting plasmid, pNB13, contained ADH1 promoter, β-galactosidase coding region and ADH1 terminator. The resulting plasmid pNB13 was used to transform yeast cells (S. cerevisiae).

Figure 9A:
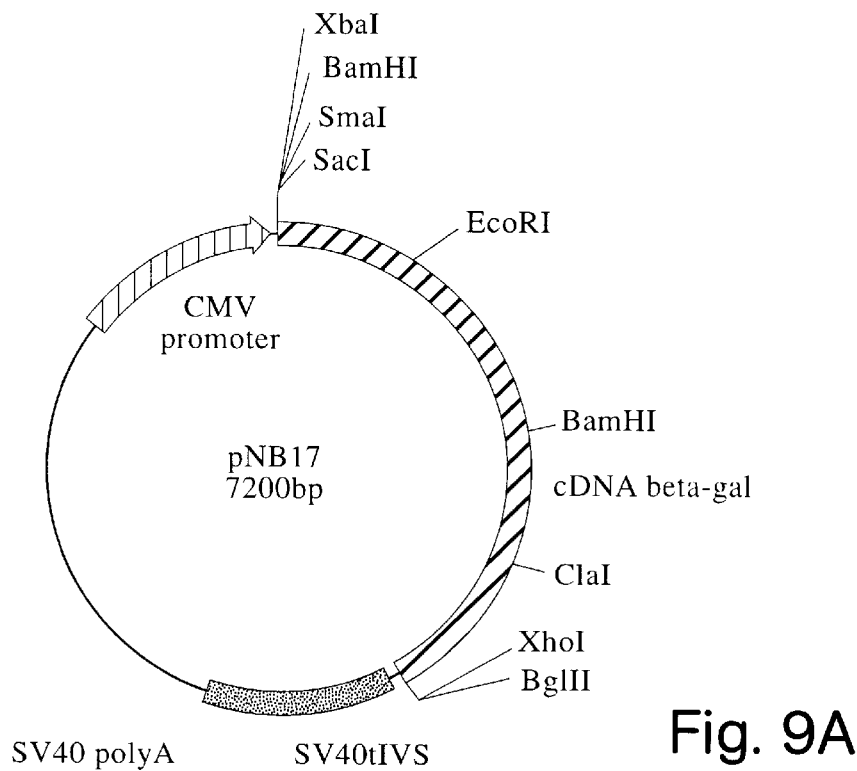
FIG. 9A is a restriction map of *A. niger* β-galactosidase mammalian expression vector pNB17.
Figure 9B:
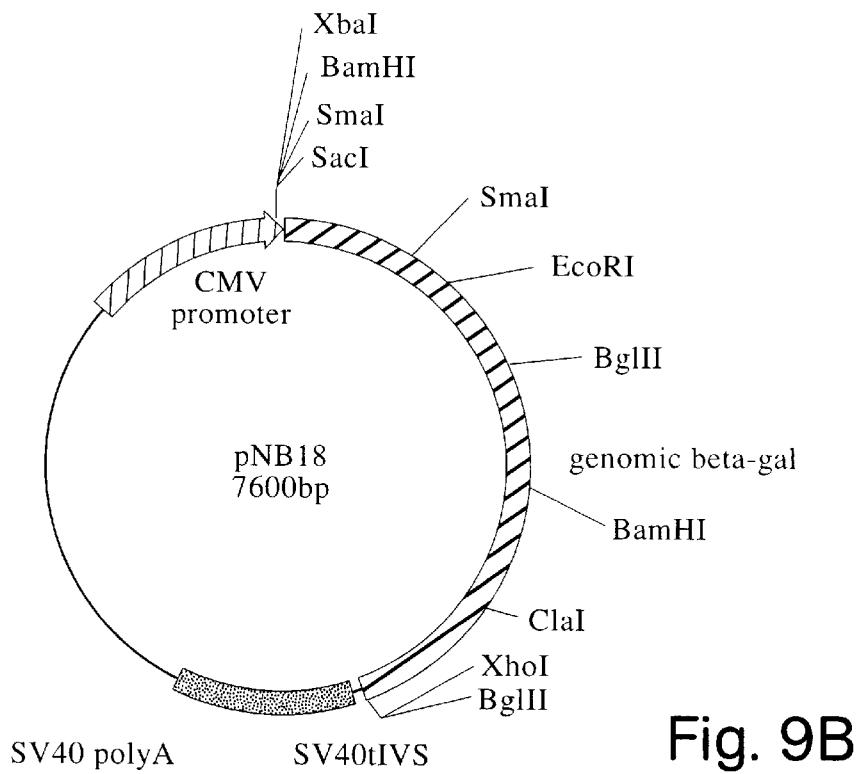
FIG. 9B is a restriction map of *A. niger* β-galactosidase mammalian expression vector pNB18.

Vectors for Expression of Recombinant A. niger β-Galactosidase in Mammalian Cells Plasmid pJ7w (ATCC no. 37724) was used to construct vectors for expression of A. niger β-galactosidase in mammalian cells. Plasmid pJ7w contained a cytomegalovirus ("CMV") promoter and its enhancer. The plasmid contained the SV40 termination sequence. Separate plasmids were constructed for expression of the A. niger β-galactosidase cDNA (pNB17; FIG. 9A) and genomic DNA (pNB18; FIG. 9B).

Mammalian expression vector pNB17 (FIG. 9A) was constructed as follows. Plasmid pJ7w was digested with SacI and BglII. A 4.2 kb DNA was purified for use as the receptor fragment. A 3 kb SacI-BglII DNA fragment containing the A. niger β-galactosidase cDNA was isolated and ligated into the 4.2 kb SacI-BglII receptor fragment obtained from pJ7w. Mammalian expression vector pNB18 was constructed according to this procedure, except that a 3 kb SacI-BglII fragment containing the A. niger β-galactosidase genomic DNA was ligated into the 4.2 kb SacI-BglII receptor fragment obtained from pJ7w.

Expression of Recombinant A. niger β-Galactosidase in E. coli

Figure 8:
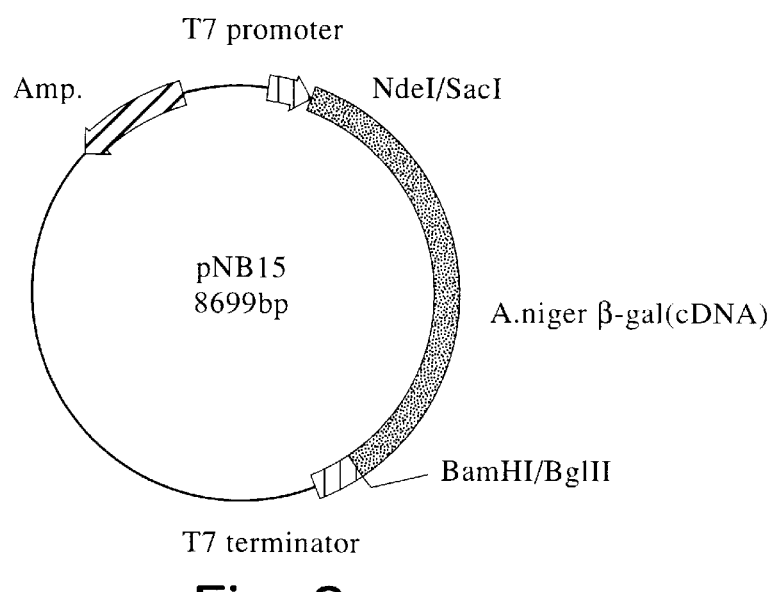
FIG. 8 is a restriction map of *A. niger* β-galactosidase bacterial expression vector pNB15.

The A. niger β-galactosidase gene was expressed in a bacterial expression system, pET (plasmid for Expression by T7 RNA polymerase; New England Biolabs). This system contains unique vectors, which were created for expression of proteins in E. coli. The A. niger β-galactosidase cDNA is placed under the control of the T7 phage promoter (pNB15; see FIG. 8) that is recognized by the phage T7 RNA polymerase but not by the bacterial RNA polymerase. FIG. 8 shows the restriction map of plasmid pNB15. Expression of the gene occurs after expression of T7 RNA polymerase which is initiated through heat induction of a second vector (pGP1-2) which has already been integrated into the genome of the bacterial strain. To assess the activity of the gene, a MUG assay was performed directly on cytoplasmic extracts. The MUG assay was performed essentially as described by Hubbes et al. (supra).

Due to the large size of the protein, i.e., 110 kDa, most of protein is found in inclusion bodies. To release the protein, in order to assess activity 5M urea was used. In addition non-denaturing gels were run on which MUG was used directly to visualize the protein within the gel. The molecular weight and biological activity of the *A. niger* β-galactosidase produced by *E. coli* was assessed using an in-gel MUG assay.

Purification and Characterization of Recombinant β-galactosidase

Following transformation, two *A. niger* strains were selected for high expression of β-galactosidase (tested by the ONPG assay). *A. niger* strains designated 8-7 and 8-18 were used for production and further analysis.

Conidia were inoculated into complete media ($10^6$/ml) and cultured at 30° C. for 6 days. Medium was collected by filtration through Miracloth™. The filtered medium was cooled to 4° C. A 50 ml sample of the filtered medium was mixed with an equal volume of isopropanol at 4° C., to precipitate β-galactosidase. After 2 hours at −20° C., the precipitate was recovered from the 50% isopropanol by centrifugation at 15,000×g for 20 minutes at 4° C. The resulting pellet was air dried and resuspended in 2 ml of 40 mM sodium acetate, pH 5.7 ("Buffer A"). Undissolved pellet was removed by an extra centrifugation step at 15000×g for 20 minutes at 4° C. The resuspended material was further dialysed against Buffer A and further purified using ion exchange chromatography.

The protein solution was applied to a DEAE-Sepharose CL-6B column equilibrated in Buffer A. The column was then washed with 50 column volumes of Buffer A. B-galactosidase was eluted from the column using 0.2M NaCl in Buffer A.

Each fraction was assayed for β-galactosidase activity using an ONPG assay. Fractions containing β-galactosidase activity were pooled. The pH of the pooled fractions was adjusted to 4.0 with acetic acid. Based on SDS-PAGE analysis and Coomassie blue staining, β-galactosidase purity was estimated to be greater than 90%.

Protein concentration of the purified enzyme was measured by a standard detergent compatible method (DC Protein Assay; Bio-Rad Laboratories, Hercules, Calif.). Bovine serum albumin was used as a standard. B-galactosidase activity was measured using a standard assay (ONPG used as a substrate analog). One unit of β-galactosidase activity was defined as hydrolysis of 1.0 μmol of ONPG per minute, at pH 4.3, at 37° C. for 10 minutes. Specific activity of the recombinant β-galactosidase at successive purification steps is shown in Table 1.

TABLE 1

Purification of recombinant β-galactosidase from A. niger

| Purification Step | Total protein (mg) | Total Activity (U) | Specific Activity U/mg | Recovery % |
|---|---|---|---|---|
| Crude media | 10.5 | 109 | 10.4 | 100 |
| Isopropanol precipitation | 2.82 | 96.8 | 34.3 | 88.8 |
| DEAE-Sepharose CL-6B | 1.77 | 92.7 | 52.4 | 95.8 |

The calculated molecular weight of the putative mature β-galactosidase deduced from cDNA is 106 kd. Based on SDS-PAGE, the molecular weight of β-galactosidase secreted by the transformed *A. niger* strain was estimated to be 144 kD. After deglycosylation, the estimated MW of the protein ranged from 100 kd to 120 kd. Western blot analysis confirmed that the 144 kD form is recognized by an antibody raised against *A. niger* β-galactosidase.

The protein band corresponding to the 144 kD protein was transferred onto PDVF membrane and its amino terminal sequence was determined by Edman degradation. The first 12 amino acid residues were determined to be ELLQKYVTWDDK (SEQ ID NO:12). This sequence corresponds to amino acid residues 40 to 51 of the sequence deduced from the cDNA. This amino terminal sequence information established the exact site for the processing of the prepro-β-galactosidase *A. niger* enzyme.

Hydrolysis Experiments

Experiments were carried to determine: (1) whether the purified recombinant protein would hydrolyze lactose in milk; (2) variation in enzyme activity in response to varying concentrations of hydrochloric acid (simulated gastric environment); and (3) variation in lactose hydrolysis rate, at varying concentrations of hydrochloric acid, as a function of enzyme concentration.

A first experiment was conducted using 10 ug and 20 ug of purified recombinant *A. niger* β-galactosidase and 200 μl of milk (1% fat), under three conditions:

(a) no added hydrochloric acid;

(b) 200 μl of hydrochloric acid (320 mM HCl, pH adjusted to 1.5 with 1N NaOH); and (c) 400 μl of hydrochloric acid.

Each of these test mixtures was incubated for 30 minutes at 37° C. The reaction was stopped by the addition of 2 ml of water and 100 μl of 3M trichloroacetic acid ("TCA"). The samples were left at room temperature for 10 to 15 minutes. The pH was adjusted to 7 with 1N NaOH, and the volume was brought to 10 ml. The samples were filtered (45 μm) and the supernatants were analyzed for lactose and galactose contents using a commercial kit (Boehringer Mannheim; cat. no. 176 303). The results are summarized in Table 2.

TABLE 2

Lactose Hydrolysis in Milk by Recombinant A. Niger β-Galactosidase.

| Amount of recombinant enzyme, μg | Volume of acid, μl | % lactose hydrolysis |
|---|---|---|
| 10 | 0 | 2.1 |
| 10 | 200 | 8.8 |
| 10 | 400 | 18.2 |
| 20 | 0 | 3.9 |
| 20 | 200 | 16.3 |
| 20 | 400 | 26.9 |

These results demonstrate that under the conditions tested, the purified recombinant enzyme hydrolyzes lactose in milk. Hydrolysis rates appear to be comparable to those of a commercial non-recombinant enzyme preparation.

A second experiment was conducted to assess variation in lactose hydrolysis rate in milk, as a function of enzyme concentration. In this experiment 200 μl of milk (1% fat) and 300 μl of 320 mM hydrochloric acid was used. The pH of the acidified milk was 4.2 (which approximates the reported pH optimum for *A. niger* β-galactosidase). Four enzyme quantities were tested: 10, 20, 40 and 80 μg. The reaction conditions were as described for experiment 1. The results are summarized in Table 3.

TABLE 3

Lactose Hydrolysis in Acidified Milk

| Amount of recombinant enzyme, ug | % lactose hydrolysis |
|---|---|
| 10 | 14.4 |
| 20 | 24.4 |
| 40 | 32.4 |
| 80 | 46.0 |

Production of A. niger Strains with Disrupted Endogenous β-Galactosidase Genes

For expression of a recombinant β-galactosidase gene in A. niger, inactivation of the endogenous β-galactosidase was desired. Two targeting molecules, i.e., plasmids pAnβpyrG1 and pAnβpyrG.6, were constructed for this purpose, using the following procedure.

The A. niger β-galactosidase genomic clone was subcloned as a 3.5 kb fragment into the XbaI/SalI digested pSP72 subcloning vector resulting to vector (pSPAnβ). The above vector (pSPAnβ) was restricted with SunI and SalI (at positions 1229 and 2391, respectively) and released a 1.2 kb internal genomic fragment. The resulting plasmid (with approximately 1 kb of β-gal flanking sequences) was treated with T4 DNA polymerase, to fill in the sticky ends.

Figure 5A:
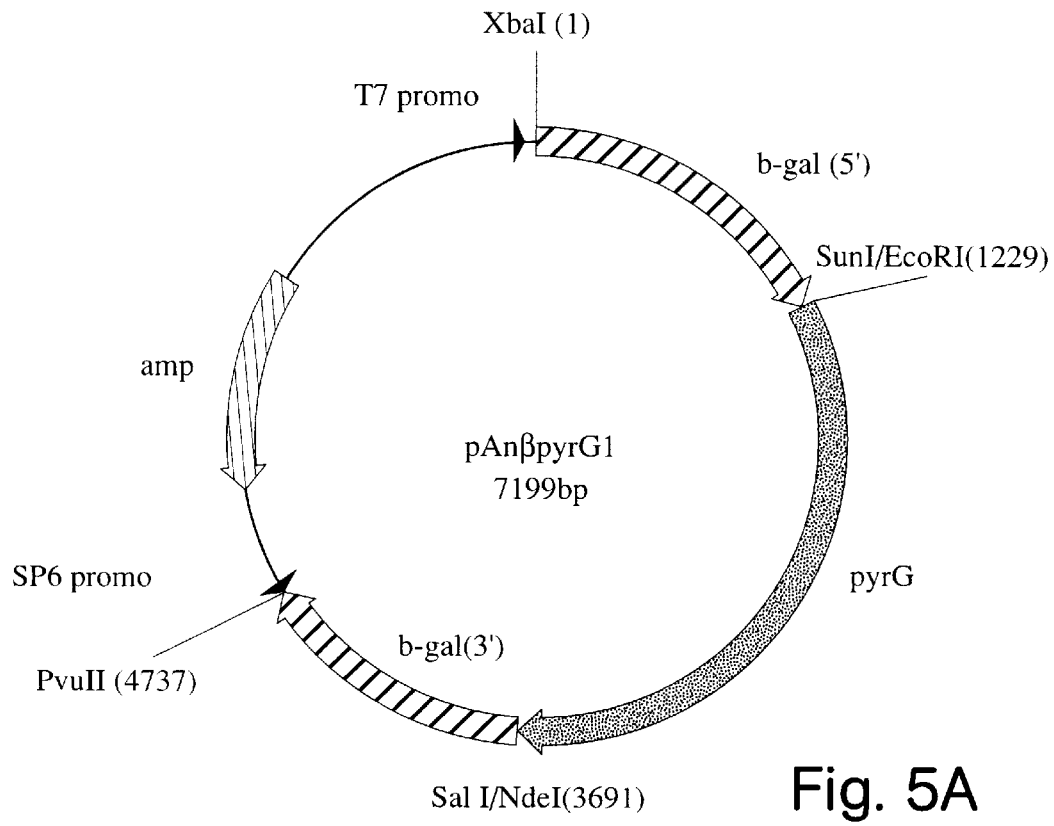
FIG. 5A is a restriction map of *A. niger* β-galactosidase targeting vector pAnβpyrG1.

The pyrG gene (2.4 kb) was isolated from plasmid pyrG (Van Hartingsvelt et al., *Mol. Gen. Genet.* 206:71–75 (1987)) by restriction with EcoRI, which cuts at the 5' end of the gene, and NdeI, which is located 200 bp downstream of the stop codon. The resulting fragment was treated with Klenow, to fill in the sticky ends. The resulting vector from above, and the pyrG fragment were ligated. Upon transformation in the *E.coli* strain DH5a transformants with the pyrG gene in the same orientation as the A. niger β-galactosidase gene (i.e., SunI to EcoRI and SalI to NdeI) were used to transform A. niger (see FIG. 5a, pSPAnβpyrG1).

Figure 5B:
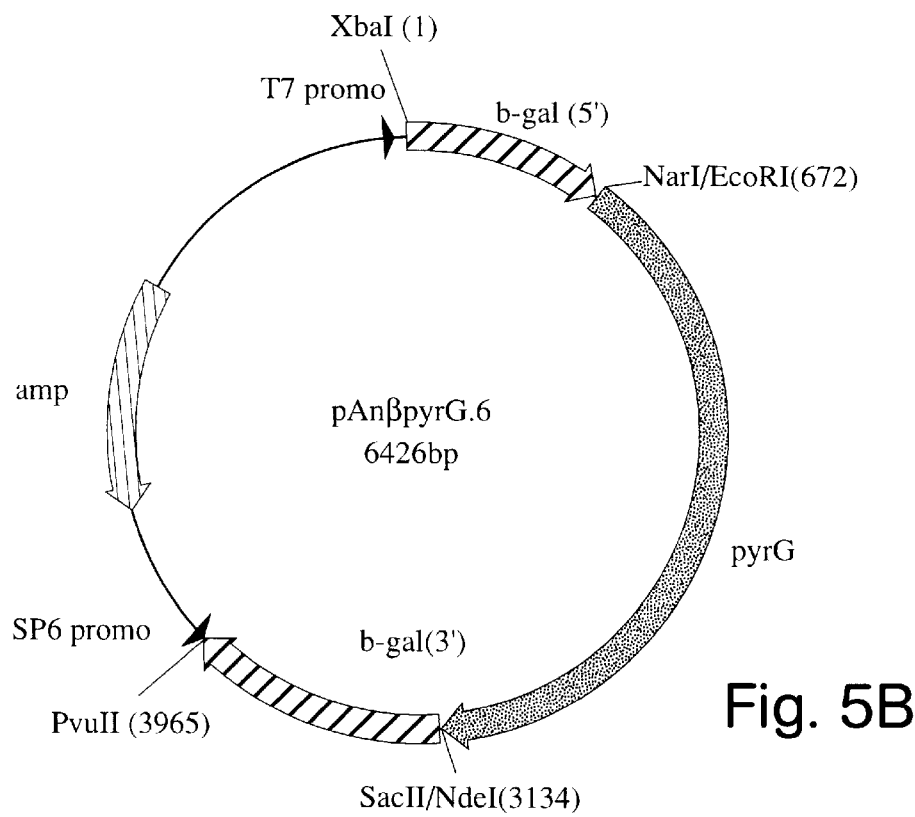
FIG. 5B is a restriction map of *A. niger* β-galactosidase targeting vector pAnβpyrG.6.

To construct the second vector, pSPAnβG.6, the same strategy was followed, except that the pSPAnβ vector was originally restricted with NarI (at position 672 in A. niger), and SacII (at position 2606). The resulting vector contains ~0.6 kb of flanking β-galactosidase sequence (see FIG. 5b, pAnβpyrG.6).

Both vectors were restricted with XbaI (5' end of the gene) and PvuII (3' end of the gene) to release the disrupted β-galactosidase insert. The linear DNA fragments were then used to transform A. niger.

Plasmids pAnβpyrG1 and pAnβpyrG.6 are used to produce a strain of A. niger with a disrupted β-galactosidase gene according to the following method.

Protoplasts from A. niger strain A920 are prepared and transformed using a modified procedure of Debets et al. (*Fungal Genetic Newsletter* 33:24 (1986)) and Werner et al (*Mol. Gen. Genet.* 209:71–77 (1987)). Conidia ($4\times10^8$) are inoculated into CM media (400 ml) and grown overnight at 30° C., 150 rpm. Mycelia are harvested by filtration through sterile Miracloth™ and added to 40 ml lytic solution (0.7M NaCl, 0.2M $CaCl_2$, pH 5.8) containing 10.0 g/ml Novozyme 234 (InterSpex Products Inc., Foster City, Calif.), and incubated at 30° C., 150 rpm for 3 hours, to generate protoplasts. Undigested mycelia are removed by filtration through sterile Miracloth™ and protoplasts were harvested by centrifugation at 3000 rpm (Beckman JA-14 rotor) at 4° C. for 5 minutes. The pellets are gently washed twice with cold SC buffer (1M sorbitol, 50 mM $CaCl_2$) and then resuspended in SC buffer at a concentration of $10^8$ protoplasts per ml. Ten μg of either pAnBpyrG1 or pAnBpyrG.6 in 10 μl sterile water is added to 0.2 ml protoplasts SC buffer and mixed with 50 ul of PEG buffer (25% w/v PEG 8000, 50 mM $CaCl_2$, 10 mM Tris-HCl, pH 7.5). The mixture is incubated on ice for 20 minutes. Then 2 mL of PEG buffer is added at room temperature and left for 5 minutes. Four ml of SC buffer is then added to the mixture and the protoplasts are harvested by centrifugation at 3000 rpm for 5 minutes at room temperature. The pellet is gently resuspended in 0.5 ml SC buffer and the aliquots of protoplasts are plated on selective plates using molten agar overlayers at 50° C.

Transformants are picked and grown in liquid cultures containing either the standard growth medium and or medium containing lactose. Cultures not growing in the lactose media are further characterized by standard molecular biology techniques.

Other embodiments are within the following claims.

---

We claim:

1. An isolated recombinant DNA molecule comprising a nucleotide sequence encoding an *Aspergillus niger* β-galactosidase polypeptide, wherein said nucleotide sequence is a cDNA sequence consisting of (SEQ ID NO:3).

2. An isolated recombinant DNA molecule comprising a nucleotide sequence which encodes the polypeptide encoded by (SEQ ID NO:4).

3. An isolated recombinant DNA molecule comprising a nucleotide sequence which consists of a genomic DNA sequence comprising an *Aspergillus niger* β-galactosidase gene which consists of (SEQ ID NO:5).

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 12 amino acids
        ( B ) TYPE: amino acid
        ( C ) STRANDEDNESS: Not Relevant
        ( D ) TOPOLOGY: both ( i i ) MOLECULE TYPE: protein ( x i ) SEQUENCE DESCRIPTION: SEQ ID NO:1:

```
Leu  Asn  Phe  Leu  Leu  Ala  Gly  Arg  Pro  Ser  Ser  Ala
 1                  5                            10
```

( 2 ) INFORMATION FOR SEQ ID NO:2:

( i ) SEQUENCE CHARACTERISTICS:
  ( A ) LENGTH: 63 amino acids
  ( B ) TYPE: amino acid
  ( C ) STRANDEDNESS: Not Relevant
  ( D ) TOPOLOGY: both ( i i ) MOLECULE TYPE: protein ( x i ) SEQUENCE DESCRIPTION: SEQ ID NO:2:

```
Gly Trp Asp Val Pro Leu Phe Leu Asn Ile Gly Asn Ser Thr Thr Pro
 1               5                  10                  15

Ser Pro Tyr Arg Val Gln Val Tyr Val Asn Gly Tyr Gln Tyr Ala Lys
             20                  25                  30

Tyr Ile Ser Asn Ile Gly Pro Gln Thr Ser Phe Pro Val Pro Glu Gly
         35                  40                  45

Ile Leu Asn Tyr Arg Gly Thr Asn Trp Leu Ala Val Thr Leu Trp
     50                  55                  60
```

( 2 ) INFORMATION FOR SEQ ID NO:3:

( i ) SEQUENCE CHARACTERISTICS:
    ( A ) LENGTH: 3057 base pairs
    ( B ) TYPE: nucleic acid
    ( C ) STRANDEDNESS: both
    ( D ) TOPOLOGY: both ( i i ) MOLECULE TYPE: cDNA ( v i ) ORIGINAL SOURCE:
    ( A ) ORGANISM: Aspergillus niger ( x i ) SEQUENCE DESCRIPTION: SEQ ID NO:3:

```
CATCATGAAG CTTTCCTCCG CTTGTGCTAT TGCCTTGCTG GCGGCACAGG CTGCTGGGGC        60
GTCCATTAAG CATCGAATCA ATGGCTTTAC CCTTACGGAG CATTCTGACC CGGCCAAGCG       120
GGAACTGTTG CAGAAATACG TCACTTGGGA TGACAAGTCC CTTTTTATCA ATGGCGAAAG       180
GATCATGATC TTCAGTGGCG AATTTCATCC ATTCCGTCTA CCTGTAAAAG AACTTCAGCT       240
TGACATCTTC CAGAAGGTCA AAGCTCTAGG GTTAACTGT GTGTCTTTCT ACGTCGATTG       300
GGCCCTCGTT GAAGGAAAAC CGGGGGAATA CAGGGCAGAC GGCATCTTTG ATTTGGAGCC       360
GTTCTTCGAC GCGGCTTCGG AAGCAGGTAT CTACCTGCTT GCCCGTCCAG GCCCGTACAT       420
CAACGCAGAG AGTTCCGGCG GTGGATTTCC GGGGTGGTTG CAGAGAGTCA ATGGTACTCT       480
TCGCTCAAGC GACAAGGCTT ACCTGGATGC TACAGATAAT TACGTCTCTC ACGTCGCTGC       540
AACAATTGCC AAGTACCAGA TTACCAATGG CGGTCCGATC ATCCTGTATC AGCCCGAAAA       600
TGAGTACACT AGTGGCTGCT GCGGTGTTGA ATTCCCCGAT CCAGTGTACA TGCAGTATGT       660
TGAAGACCAG GCTCGTAACG CCGGTGTCGT CATTCCATTG ATCAATAACG ATGCCTCGGC       720
TTCCGGGAAC AATGCTCCTG GAACCGGGAA GGGAGCAGTC GATATTTACG CCATGATAG       780
CTACCCGCTT GGGTTCGACT GCGCGAACCC TACGGTATGG CCCTCGGGTG ACCTACCTAC       840
CAATTTCCGT ACCCTTCATC TTGAGCAAAG CCCGACCACA CCATATGCGA TAGTCGAGTT       900
CCAAGGCGGT TCGTACGACC CTTGGGGAGG ACCGGGATTC GCTGCGTGCT CCGAACTCCT       960
GAACAATGAG TTCGAGAGAG TGTTCTATAA GAACGACTTT AGCTTCCAGA TTGCCATTAT      1020
GAACCTCTAC ATGATCTTTG GTGGAACTAA CTGGGGTAAC CTCGGTTATC CTAATGGATA      1080
CACCTCCTAC GACTATGGTT CGGCTGTGAC AGAATCTCGC AACATCACCC GCGAGAAATA      1140
CAGTGAACTC AAGCTACTTG GCAACTTTGC CAAAGTATCT CCGGGCTATT TGACGGCTAG      1200
TCCTGGCAAT TTGACAACTT CCGGTTACGC TGATACCACA GACCTGACTG TAACGCCTTT      1260
```

-continued

| | | | | | |
|---|---|---|---|---|---|
| GCTCGGAAAC | AGCACTGGCT | CTTTCTTCGT | GGTCAGACAT | TCGGACTACA | GCAGCGAAGA | 1320 |
| GTCAACATCA | TACAAGCTTC | GTCTTCCTAC | CAGTGCCGGT | AGCGTGACTA | TCCCTCAGCT | 1380 |
| TGGTGGTACA | CTCACACTTA | ATGGACGCGA | TTCAAAGATA | CACGTGACCG | ACTACAATGT | 1440 |
| CTCTGGAACC | AATATCATCT | ACTCCACGGC | CGAGGTCTTT | ACCTGGAAGA | AGTTCGCCGA | 1500 |
| CGGAAAGGTC | CTCGTGCTCT | ACGGAGGTGC | TGGTGAGCAC | CACGAACTTG | CCATTTCAAC | 1560 |
| CAAGTCGAAT | GTCACGGTGA | TTGAAGGATC | CGAGTCTGGC | ATCTCGTCAA | AGCAGACCTC | 1620 |
| TTCGTCAGTT | GTGGTCGGCT | GGGATGTGTC | GACCACTCGT | CGTATCATCC | AAGTTGGGGA | 1680 |
| CCTGAAAATT | CTCCTTCTTG | ACAGGAACTC | TGCCTATAAC | TACTGGGTGC | CTCAACTTGC | 1740 |
| CACAGACGGC | ACTTCACCAG | GTTTTAGCAC | CCCAGAGAAG | GTCGCATCAT | CCATCATCGT | 1800 |
| CAAAGCGGGC | TACCTTGTTC | GGACTGCGTA | CCTGAAGGGC | AGCGGTCTTT | ACCTCACCGC | 1860 |
| AGACTTCAAC | GCTACCACTT | CCGTTGAAGT | CATTGGCGTC | CCCTCCACTG | CTAAGAATCT | 1920 |
| GTTCATCAAT | GGAGATAAGA | CATCGCACAC | CGTCGACAAG | AACGGCATCT | GGTCAGCTAC | 1980 |
| AGTCGACTAC | AATGCCCCTG | ATATCTCGCT | TCCCAGCCTG | AAGGACTTGG | ACTGGAAGTA | 2040 |
| CGTGGACACT | CTTCCGGAGA | TCCAGTCCTC | CTACGATGAT | TCTCTCTGGC | CCGCCGCAGA | 2100 |
| CCTCAAGCAG | ACCAAGAATA | CGCTTCGTTC | TCTGACGACC | CCTACCTCTC | TGTACTCATC | 2160 |
| CGATTACGGC | TTCCACACCG | GATACCTGCT | TTACCGCGGA | CACTTCACCG | CCACGGGCAA | 2220 |
| CGAGAGCACC | TTTGCTATCG | ATACGCAAGG | TGGATCAGCA | TTTGGAAGCT | CTGTCTGGCT | 2280 |
| GAACGGAACA | TACCTCGGTT | CCTGGACTGG | CCTTTATGCC | AACTCCGACT | ACAATGCCAC | 2340 |
| TTACAATCTG | CCTCAGCTCC | AGGCAGGCAA | GACGTATGTG | ATCACCGTTG | TGATCGACAA | 2400 |
| CATGGGCCTT | GAGGAGAACT | GGACTGTTGG | TGAGGACCTA | ATGAAGACCC | CGCGTGGTAT | 2460 |
| TCTCAACTTC | CTGCTTGCCG | GACGGCCAAG | CAGCGCAATT | AGCTGGAAGT | TGACCGGAAA | 2520 |
| CCTTGGCGGC | GAGGACTACG | AAGACAAGGT | CCGAGGTCCT | CTGAACGAGG | GTGGTCTCTA | 2580 |
| CGCTGAGCGC | CAAGGATTTC | ACCAGCCCGA | GCCTCCCAGC | CAGAACTGGA | AGTCTTCCAG | 2640 |
| CCCTCTGGAG | GGTCTCTCTG | AGGCAGGCAT | TGGTTTCTAC | AGCGCCAGTT | TTGACCTTGA | 2700 |
| CCTGCCGAAG | GGATGGGATG | TCCCACTGTT | CCTCAACATC | GGTAACAGCA | CTACGCCATC | 2760 |
| CCCGTACCGC | GTGCAGGTCT | ACGTCAACGG | ATATCAGTAT | GCGAAATACA | TAAGCAACAT | 2820 |
| CGGACCTCAG | ACCAGCTTCC | CTGTCCCCGA | GGGAATCCTG | AACTATCGCG | GAACGAACTG | 2880 |
| GTTGGCGGTG | ACCCTGTGGG | CTCTCGACTC | TGCCGGCGGC | AAGTTGGAAA | GCTTGGAGTT | 2940 |
| GAGTTACACC | ACTCCAGTGC | TGACTGCCCT | TGGGGAGGTC | GAGTCGGTTG | ACCAGCCCAA | 3000 |
| GTACAAGAAG | CGGAAGGGTG | CATACTAGGT | TCTGTAAATA | GCACATTCTA | TCTAGTT | 3057 |

( 2 ) INFORMATION FOR SEQ ID NO:4:

( i ) SEQUENCE CHARACTERISTICS:
  ( A ) LENGTH: 1007 amino acids
  ( B ) TYPE: amino acid
  ( D ) TOPOLOGY: linear ( i i ) MOLECULE TYPE: protein ( x i ) SEQUENCE DESCRIPTION: SEQ ID NO:4:

```
Met  Lys  Leu  Ser  Ser  Ala  Cys  Ala  Ile  Ala  Leu  Leu  Ala  Ala  Gln  Ala
 1                 5                        10                           15

Ala  Gly  Ala  Ser  Ile  Lys  His  Arg  Ile  Asn  Gly  Phe  Thr  Leu  Thr  Glu
                    20                       25                     30

His  Ser  Asp  Pro  Ala  Lys  Arg  Glu  Leu  Leu  Gln  Lys  Tyr  Val  Thr  Trp
                35                       40                    45
```

| | | | | | | | | | | | | | | |
|---|---|---|---|---|---|---|---|---|---|---|---|---|---|---|
|Asp|Asp|Lys|Ser|Leu|Phe|Ile|Asn|Gly|Glu|Arg|Ile|Met|Ile|Phe|Ser|
| |50| | | |55| | | |60| | | | | |
|Gly|Glu|Phe|His|Pro|Phe|Arg|Leu|Pro|Val|Lys|Glu|Leu|Gln|Leu|Asp|
|65| | | |70| | | |75| | | | | | |80|
|Ile|Phe|Gln|Lys|Val|Lys|Ala|Leu|Gly|Phe|Asn|Cys|Val|Ser|Phe|Tyr|
| | | | |85| | | | |90| | | | |95| |
|Val|Asp|Trp|Ala|Leu|Val|Glu|Gly|Lys|Pro|Gly|Glu|Tyr|Arg|Ala|Asp|
| | | |100| | | | |105| | | |110| | | |
|Gly|Ile|Phe|Asp|Leu|Glu|Pro|Phe|Phe|Asp|Ala|Ala|Ser|Glu|Ala|Gly|
| | |115| | | |120| | | |125| | | | | |
|Ile|Tyr|Leu|Leu|Ala|Arg|Pro|Gly|Pro|Tyr|Ile|Asn|Ala|Glu|Ser|Ser|
| |130| | | | |135| | | |140| | | | | |
|Gly|Gly|Gly|Phe|Pro|Gly|Trp|Leu|Gln|Arg|Val|Asn|Gly|Thr|Leu|Arg|
|145| | | |150| | | | |155| | | | | |160|
|Ser|Ser|Asp|Lys|Ala|Tyr|Leu|Asp|Ala|Thr|Asp|Asn|Tyr|Val|Ser|His|
| | | |165| | | |170| | | |175| | | | |
|Val|Ala|Ala|Thr|Ile|Ala|Lys|Tyr|Gln|Ile|Thr|Asn|Gly|Gly|Pro|Ile|
| | | |180| | | |185| | | |190| | | | |
|Ile|Leu|Tyr|Gln|Pro|Glu|Asn|Glu|Tyr|Thr|Ser|Gly|Cys|Cys|Gly|Val|
| | |195| | | |200| | | |205| | | | | |
|Glu|Phe|Pro|Asp|Pro|Val|Tyr|Met|Gln|Tyr|Val|Glu|Asp|Gln|Ala|Arg|
| |210| | | |215| | | |220| | | | | | |
|Asn|Ala|Gly|Val|Val|Ile|Pro|Leu|Ile|Asn|Asn|Asp|Ala|Ser|Ala|Ser|
|225| | | |230| | | |235| | | |240| | | |
|Gly|Asn|Asn|Ala|Pro|Gly|Thr|Gly|Lys|Gly|Ala|Val|Asp|Ile|Tyr|Gly|
| | | |245| | | |250| | | |255| | | | |
|His|Asp|Ser|Tyr|Pro|Leu|Gly|Phe|Asp|Cys|Ala|Asn|Pro|Thr|Val|Trp|
| | | |260| | | |265| | | |270| | | | |
|Pro|Ser|Gly|Asp|Leu|Pro|Thr|Asn|Phe|Arg|Thr|Leu|His|Leu|Glu|Gln|
| | |275| | | |280| | | |285| | | | | |
|Ser|Pro|Thr|Thr|Pro|Tyr|Ala|Ile|Val|Glu|Phe|Gln|Gly|Gly|Ser|Tyr|
| |290| | | |295| | | |300| | | | | | |
|Asp|Pro|Trp|Gly|Gly|Pro|Gly|Phe|Ala|Ala|Cys|Ser|Glu|Leu|Leu|Asn|
|305| | | |310| | | |315| | | |320| | | |
|Asn|Glu|Phe|Glu|Arg|Val|Phe|Tyr|Lys|Asn|Asp|Phe|Ser|Phe|Gln|Ile|
| | | |325| | | |330| | | |335| | | | |
|Ala|Ile|Met|Asn|Leu|Tyr|Met|Ile|Phe|Gly|Gly|Thr|Asn|Trp|Gly|Asn|
| | |340| | | |345| | | |350| | | | | |
|Leu|Gly|Tyr|Pro|Asn|Gly|Tyr|Thr|Ser|Tyr|Asp|Tyr|Gly|Ser|Ala|Val|
| | |355| | | |360| | | |365| | | | | |
|Thr|Glu|Ser|Arg|Asn|Ile|Thr|Arg|Glu|Lys|Tyr|Ser|Glu|Leu|Lys|Leu|
|370| | | | |375| | | |380| | | | | | |
|Leu|Gly|Asn|Phe|Ala|Lys|Val|Ser|Pro|Gly|Tyr|Leu|Thr|Ala|Ser|Pro|
|385| | | |390| | | | |395| | | | | |400|
|Gly|Asn|Leu|Thr|Thr|Ser|Gly|Tyr|Ala|Asp|Thr|Thr|Asp|Leu|Thr|Val|
| | | |405| | | |410| | | |415| | | | |
|Thr|Pro|Leu|Leu|Gly|Asn|Ser|Thr|Gly|Ser|Phe|Phe|Val|Val|Arg|His|
| | |420| | | |425| | | |430| | | | | |
|Ser|Asp|Tyr|Ser|Ser|Glu|Glu|Ser|Thr|Ser|Tyr|Lys|Leu|Arg|Leu|Pro|
| | |435| | | |440| | | |445| | | | | |
|Thr|Ser|Ala|Gly|Ser|Val|Thr|Ile|Pro|Gln|Leu|Gly|Gly|Thr|Leu|Thr|
| |450| | | |455| | | |460| | | | | | |
|Leu|Asn|Gly|Arg|Asp|Ser|Lys|Ile|His|Val|Thr|Asp|Tyr|Asn|Val|Ser|

```
        465                      470                      475                      480
Gly  Thr  Asn  Ile  Ile  Tyr  Ser  Thr  Ala  Glu  Val  Phe  Thr  Trp  Lys  Lys
                    485                      490                      495

Phe  Ala  Asp  Gly  Lys  Val  Leu  Val  Leu  Tyr  Gly  Gly  Ala  Gly  Glu  His
               500                      505                      510

His  Glu  Leu  Ala  Ile  Ser  Thr  Lys  Ser  Asn  Val  Thr  Val  Ile  Glu  Gly
          515                      520                      525

Ser  Glu  Ser  Gly  Ile  Ser  Ser  Lys  Gln  Thr  Ser  Ser  Ser  Val  Val  Val
     530                      535                      540

Gly  Trp  Asp  Val  Ser  Thr  Thr  Arg  Arg  Ile  Ile  Gln  Val  Gly  Asp  Leu
545                      550                      555                      560

Lys  Ile  Leu  Leu  Leu  Asp  Arg  Asn  Ser  Ala  Tyr  Asn  Tyr  Trp  Val  Pro
                    565                      570                      575

Gln  Leu  Ala  Thr  Asp  Gly  Thr  Ser  Pro  Gly  Phe  Ser  Thr  Pro  Glu  Lys
               580                      585                      590

Val  Ala  Ser  Ser  Ile  Ile  Val  Lys  Ala  Gly  Tyr  Leu  Val  Arg  Thr  Ala
          595                      600                      605

Tyr  Leu  Lys  Gly  Ser  Gly  Leu  Tyr  Leu  Thr  Ala  Asp  Phe  Asn  Ala  Thr
     610                      615                      620

Thr  Ser  Val  Glu  Val  Ile  Gly  Val  Pro  Ser  Thr  Ala  Lys  Asn  Leu  Phe
625                      630                      635                      640

Ile  Asn  Gly  Asp  Lys  Thr  Ser  His  Thr  Val  Asp  Lys  Asn  Gly  Ile  Trp
                    645                      650                      655

Ser  Ala  Thr  Val  Asp  Tyr  Asn  Ala  Pro  Asp  Ile  Ser  Leu  Pro  Ser  Leu
               660                      665                      670

Lys  Asp  Leu  Asp  Trp  Lys  Tyr  Val  Asp  Thr  Leu  Pro  Glu  Ile  Gln  Ser
          675                      680                      685

Ser  Tyr  Asp  Asp  Ser  Leu  Trp  Pro  Ala  Ala  Asp  Leu  Lys  Gln  Thr  Lys
     690                      695                      700

Asn  Thr  Leu  Arg  Ser  Leu  Thr  Thr  Pro  Thr  Ser  Leu  Tyr  Ser  Ser  Asp
705                      710                      715                      720

Tyr  Gly  Phe  His  Thr  Gly  Tyr  Leu  Leu  Tyr  Arg  Gly  His  Phe  Thr  Ala
                    725                      730                      735

Thr  Gly  Asn  Glu  Ser  Thr  Phe  Ala  Ile  Asp  Thr  Gln  Gly  Gly  Ser  Ala
               740                      745                      750

Phe  Gly  Ser  Ser  Val  Trp  Leu  Asn  Gly  Thr  Tyr  Leu  Gly  Ser  Trp  Thr
          755                      760                      765

Gly  Leu  Tyr  Ala  Asn  Ser  Asp  Tyr  Asn  Ala  Thr  Tyr  Asn  Leu  Pro  Gln
     770                      775                      780

Leu  Gln  Ala  Gly  Lys  Thr  Tyr  Val  Ile  Thr  Val  Val  Ile  Asp  Asn  Met
785                      790                      795                      800

Gly  Leu  Glu  Glu  Asn  Trp  Thr  Val  Gly  Glu  Asp  Leu  Met  Lys  Thr  Pro
                    805                      810                      815

Arg  Gly  Ile  Leu  Asn  Phe  Leu  Leu  Ala  Gly  Arg  Pro  Ser  Ser  Ala  Ile
               820                      825                      830

Ser  Trp  Lys  Leu  Thr  Gly  Asn  Leu  Gly  Gly  Glu  Asp  Tyr  Glu  Asp  Lys
          835                      840                      845

Val  Arg  Gly  Pro  Leu  Asn  Glu  Gly  Gly  Leu  Tyr  Ala  Glu  Arg  Gln  Gly
     850                      855                      860

Phe  His  Gln  Pro  Glu  Pro  Pro  Ser  Gln  Asn  Trp  Lys  Ser  Ser  Ser  Pro
865                      870                      875                      880

Leu  Glu  Gly  Leu  Ser  Glu  Ala  Gly  Ile  Gly  Phe  Tyr  Ser  Ala  Ser  Phe
                    885                      890                      895
```

| | | | | | | | | | | | | | | |
|---|---|---|---|---|---|---|---|---|---|---|---|---|---|---|
| Asp | Leu | Asp | Leu | Pro | Lys | Gly | Trp | Asp | Val | Pro | Leu | Phe | Leu | Asn | Ile |
| | | | 900 | | | | 905 | | | | | 910 | | |
| Gly | Asn | Ser | Thr | Thr | Pro | Ser | Pro | Tyr | Arg | Val | Gln | Val | Tyr | Val | Asn |
| | | | 915 | | | | 920 | | | | 925 | | | |
| Gly | Tyr | Gln | Tyr | Ala | Lys | Tyr | Ile | Ser | Asn | Ile | Gly | Pro | Gln | Thr | Ser |
| | 930 | | | | | 935 | | | | | 940 | | | | |
| Phe | Pro | Val | Pro | Glu | Gly | Ile | Leu | Asn | Tyr | Arg | Gly | Thr | Asn | Trp | Leu |
| 945 | | | | | 950 | | | | | 955 | | | | | 960 |
| Ala | Val | Thr | Leu | Trp | Ala | Leu | Asp | Ser | Ala | Gly | Gly | Lys | Leu | Glu | Ser |
| | | | | 965 | | | | | 970 | | | | | 975 | |
| Leu | Glu | Leu | Ser | Tyr | Thr | Thr | Pro | Val | Leu | Thr | Ala | Leu | Gly | Glu | Val |
| | | | 980 | | | | | 985 | | | | | 990 | | |
| Glu | Ser | Val | Asp | Gln | Pro | Lys | Tyr | Lys | Lys | Arg | Lys | Gly | Ala | Tyr | |
| | | 995 | | | | | 1000 | | | | | 1005 | | | |

(2) INFORMATION FOR SEQ ID NO:5:

(i) SEQUENCE CHARACTERISTICS:
        (A) LENGTH: 3466 base pairs
        (B) TYPE: nucleic acid
        (C) STRANDEDNESS: both
        (D) TOPOLOGY: both (ii) MOLECULE TYPE: DNA (genomic)

(vi) ORIGINAL SOURCE:
        (A) ORGANISM: Aspergillus niger (xi) SEQUENCE DESCRIPTION: SEQ ID NO:5:

```
CATCATGAAG CTTTCCTCCG CTTGTGCTAT TGCCTTGCTG GCGGCACAGG CTGCTGGGGC        60
GTCCATTAAG CATCGAATCA ATGGCTTTAC CCTTACGGAG CATTCTGACC CGGCCAAGCG       120
GGAACTGTTG CAGAAATACG TATGTACGTC CATGGATGGA AGCACTTCTA GCAAACTGAC       180
ATAGTGCCTA CTAGGTCACT TGGGATGACA AGTCCCTTTT TATCAATGGC GAAAGGATCA       240
TGATCTTCAG TGGCGAATTT CATCCATTCC GGTACTACAG CCCTTCCTTC TTCTATCTAT       300
ACTGAGGTGG ACTCGGGATT TTTTTTGGAT TGCTCTAGTC TACCTGTAAA AGAACTTCAG       360
CTTGACATCT TCCAGAAGGT CAAAGCTCTA GGGTTTAACT GTGTGTCTTT CTACGTCGAT       420
TGGGCCCTCG TTGAAGGAAA ACCGGGGGAA TACAGGGCAG ACGGCATCTT TGATTTGGAG       480
CCGTTCTTCG ACGCGGCTTC GGAAGCAGGT ATCTACCTGC TTGCCCGTCC AGGCCCGTAC       540
ATCAACGCAG AGAGTTCCGG CGGTGGATTT CCGGGGTGGT TGCAGAGAGT CAATGGTACT       600
CTTCGCTCAA GCGACAAGGC TTACCTGGAT GCTACAGATA AGTATGGTGA AACTCGCCCG       660
GGAGGCCTAT GGCGCCTGCT GACTTTTCCA CAGTTACGTC TCTCACGTCG CTGCAACAAT       720
TGCCAAGTAC CAGATTACCA ATGGCGGTCC GATCATCCTG TATCAGCCCG AAAATGAGTA       780
CACTAGTGGC TGCTGCGGTG TTGAATTCCC CGATCCAGTG TACATGCAGT ATGTTGAAGA       840
CCAGGCTCGT AACGCCGGTG TCGTCATTCC ATTGATCAAT AACGATGCCT CGGCTTCCGG       900
GAACAATGCT CCTGGAACCG GGAAGGGAGC AGTCGATATT TACGGCATG ATAGCTACCC       960
GTAAGTTCAG CATGCCCTTG ACTGTGAACA CTGGCTGACA ATCATAGGCT TGGGTTCGAC      1020
TGCGTATGTT TATTCTTGAG TCTCGGTGTG CTTGTAGCTA ATTTGTCTAG GCGAACCCTA      1080
CGGTATGGCC CTCGGGTGAC CTACCTACCA ATTTCCGTAC CCTTCATCTT GAGCAAAGCC      1140
CGACCACACC ATATGCGATA GTCGAGGTCA GTATATACGT ACTCTAGTCA GCATTGGGG      1200
GCTAACACCT CGCAGTTCCA AGGCGGTTCG TACGACCCTT GGGGAGGACC GGGATTCGCT      1260
GCGTGCTCCG AACTCCTGAA CAATGAGTTC GAGAGAGTGT TCTATAAGAA CGACTTTAGC      1320
```

-continued

```
TTCCAGATTG  CCATTATGAA  CCTCTACATG  GTACGTGCAT  GGATTTTTAC  GCTGGATTGC    1380
AGCTAATATG  TGTAGATCTT  TGGTGGAACT  AACTGGGGTA  ACCTCGGTTA  TCCTAATGGA    1440
TACACCTCCT  ACGACTATGG  TTCGGCTGTG  ACAGAATCTC  GCAACATCAC  CCGCGAGAAA    1500
TACAGTGAAC  TCAAGCTACT  TGGCAACTTT  GCCAAAGTAT  CTCCGGGCTA  TTTGACGGCT    1560
AGTCCTGGCA  ATTTGACAAC  TTCCGGTTAC  GCTGATACCA  CAGACCTGAC  TGTAACGCCT    1620
TTGCTCGGAA  ACAGCACTGG  CTCTTTCTTC  GTGGTCAGAC  ATTCGGACTA  CAGCAGCGAA    1680
GAGTCAACAT  CATACAAGCT  TCGTCTTCCT  ACCAGTGCCG  GTAGCGTGAC  TATCCCTCAG    1740
CTTGGTGGTA  CACTCACACT  TAATGGACGC  GATTCAAAGA  TACACGTGAC  CGACTACAAT    1800
GTCTCTGGAA  CCAATATCAT  CTACTCCACG  GCCGAGGTCT  TACCTGGAA   GAAGTTCGCC    1860
GACGGAAAGG  TCCTCGTGCT  CTACGGAGGT  GCTGGTGAGC  ACCACGAACT  TGCCATTTCA    1920
ACCAAGTCGA  ATGTACGGT   GATTGAAGGA  TCCGAGTCTG  GCATCTCGTC  AAAGCAGACC    1980
TCTTCGTCAG  TTGTGGTCGG  CTGGGATGTG  TCGACCACTC  GTCGTATCAT  CCAAGTTGGG    2040
GACCTGAAAA  TTCTCCTTCT  TGGTAGGTCC  ATCCAACTGT  CCGAGTTACA  TCAAGCTGAC    2100
TAGTATCAGA  CAGGAACTCT  GCCTATAACT  ACTGGGTGCC  TCAACTTGCC  ACAGACGGCA    2160
CTTCACCAGG  TTTTAGCACC  CCAGAGAAGG  TCGCATCATC  CATCATCGTC  AAAGCGGGCT    2220
ACCTTGTTCG  GACTGCGTAC  CTGAAGGGCA  GCGGTCTTTA  CCTCACCGCA  GACTTCAACG    2280
CTACCACTTC  CGTTGAAGTC  ATTGGCGTCC  CCTCCACTGC  TAAGAATCTG  TTCATCAATG    2340
GAGATAAGAC  ATCGCACACC  GTCGACAAGA  ACGGCATCTG  GTCAGCTACA  GTCGACTACA    2400
ATGCCCCTGA  TATCTCGCTT  CCCAGCCTGA  AGGACTTGGA  CTGGAAGTAC  GTGGACACTC    2460
TTCCGGAGAT  CCAGTCCTCC  TACGATGATT  CTCTCTGGCC  CGCCGCAGAC  CTCAAGCAGA    2520
CCAAGAATAC  GCTTCGTTCT  CTGACGACCC  CTACCTCTCT  GTACTCATCC  GATTACGGCT    2580
TCCACACCGG  ATACCTGCTT  TACCGCGGAC  ACTTCACCGC  CACGGGCAAC  GAGAGCACCT    2640
TTGCTATCGA  TACGCAAGGT  GGATCAGCAT  TTGGAAGCTC  TGTCTGGCTG  AACGGAACAT    2700
ACCTCGGTTC  CTGGACTGGC  CTTTATGCCA  ACTCCGACTA  CAATGCCACT  TACAATCTGC    2760
CTCAGCTCCA  GGCAGGCAAG  ACGTATGTGA  TCACCGTTGT  GATCGACAAC  ATGGGCCTTG    2820
AGGAGAACTG  GACTGTTGGT  GAGGACCTAA  TGAAGACCCC  GCGTGGTATT  CTCAACTTCC    2880
TGCTTGCCGG  ACGGCCAAGC  AGCGCAATTA  GCTGGAAGTT  GACCGGAAAC  CTTGGCGGCG    2940
AGGACTACGA  AGACAAGGTC  CGAGGTCCTC  TGAACGAGGG  TGGTCTCTAC  GCTGAGCGCC    3000
AAGGATTTCA  CCAGCCCGAG  CCTCCCAGCC  AGAACTGGAA  GTCTTCCAGC  CCTCTGGAGG    3060
GTCTCTCTGA  GGCAGGCATT  GGTTTCTACA  GCGCCAGTTT  TGACCTTGAC  CTGCCGAAGG    3120
GATGGGATGT  CCCACTGTTC  CTCAACATCG  GTAACAGCAC  TACGCCATCC  CCGTACCGCG    3180
TGCAGGTCTA  CGTCAACGGA  TATCAGTATG  CGAAATACAT  AAGCAACATC  GGACCTCAGA    3240
CCAGCTTCCC  TGTCCCCGAG  GGAATCCTGA  ACTATCGCGG  AACGAACTGG  TTGGCGGTGA    3300
CCCTGTGGGC  TCTCGACTCT  GCCGGCGGCA  AGTTGGAAAG  CTTGGAGTTG  AGTTACACCA    3360
CTCCAGTGCT  GACTGCCCTT  GGGGAGGTCG  AGTCGGTTGA  CCAGCCCAAG  TACAAGAAGC    3420
GGAAGGGTGC  ATACTAGGTT  CTGTAAATAG  CACATTCTAT  CTAGTT                    3466
```

(2) INFORMATION FOR SEQ ID NO:6:

(i) SEQUENCE CHARACTERISTICS:
        (A) LENGTH: 32 base pairs
        (B) TYPE: nucleic acid
        (C) STRANDEDNESS: both ( D ) TOPOLOGY: both ( i i ) MOLECULE TYPE: cDNA ( v i ) ORIGINAL SOURCE:
    ( A ) ORGANISM: Aspergillus niger ( x i ) SEQUENCE DESCRIPTION: SEQ ID NO:6:

ATTAGAGCTC ATGAAGCTTT CCTCCGCTTG TG　　　　　　　　　　　　32

( 2 ) INFORMATION FOR SEQ ID NO:7:

( i ) SEQUENCE CHARACTERISTICS:
        ( A ) LENGTH: 36 base pairs
        ( B ) TYPE: nucleic acid
        ( C ) STRANDEDNESS: both
        ( D ) TOPOLOGY: both ( i i ) MOLECULE TYPE: cDNA ( v i ) ORIGINAL SOURCE:
        ( A ) ORGANISM: Aspergillus niger ( x i ) SEQUENCE DESCRIPTION: SEQ ID NO:7:

ATTAAGATCT CGAGAATGTG CTATTTACAG AACCTA　　　　　　　36

( 2 ) INFORMATION FOR SEQ ID NO:8:

( i ) SEQUENCE CHARACTERISTICS:
        ( A ) LENGTH: 35 base pairs
        ( B ) TYPE: nucleic acid
        ( C ) STRANDEDNESS: both
        ( D ) TOPOLOGY: both ( i i ) MOLECULE TYPE: cDNA ( v i ) ORIGINAL SOURCE:
        ( A ) ORGANISM: Aspergillus niger ( x i ) SEQUENCE DESCRIPTION: SEQ ID NO:8:

GAGTCTAGAT ACAATGAAGC TTTCCTCCGC TTGTG　　　　　　　35

( 2 ) INFORMATION FOR SEQ ID NO:9:

( i ) SEQUENCE CHARACTERISTICS:
        ( A ) LENGTH: 36 base pairs
        ( B ) TYPE: nucleic acid
        ( C ) STRANDEDNESS: both
        ( D ) TOPOLOGY: both ( i i ) MOLECULE TYPE: cDNA ( v i ) ORIGINAL SOURCE:
        ( A ) ORGANISM: Aspergillus niger ( x i ) SEQUENCE DESCRIPTION: SEQ ID NO:9:

ATTAAGATCT CGAGAATGTG CTATTTACAG AACCTA　　　　　　　36

( 2 ) INFORMATION FOR SEQ ID NO:10:

( i ) SEQUENCE CHARACTERISTICS:
        ( A ) LENGTH: 29 base pairs
        ( B ) TYPE: nucleic acid
        ( C ) STRANDEDNESS: both
        ( D ) TOPOLOGY: both ( i i ) MOLECULE TYPE: cDNA ( v i ) ORIGINAL SOURCE:
        ( A ) ORGANISM: Aspergillus niger ( x i ) SEQUENCE DESCRIPTION: SEQ ID NO:10:

-continued

```
TTAGGTACCT CGAGGATTGT CTGAACATT                                                      29
```

( 2 ) INFORMATION FOR SEQ ID NO:11:

( i ) SEQUENCE CHARACTERISTICS:
        ( A ) LENGTH: 28 base pairs
        ( B ) TYPE: nucleic acid
        ( C ) STRANDEDNESS: both
        ( D ) TOPOLOGY: both ( i i ) MOLECULE TYPE: cDNA ( v i ) ORIGINAL SOURCE:
        ( A ) ORGANISM: Aspergillus niger ( x i ) SEQUENCE DESCRIPTION: SEQ ID NO:11:

```
GCGTCTAGAG GTGTAATGAT GCTGGGGA                                                       28
```

( 2 ) INFORMATION FOR SEQ ID NO:12:

( i ) SEQUENCE CHARACTERISTICS:
        ( A ) LENGTH: 12 amino acids
        ( B ) TYPE: amino acid
        ( C ) STRANDEDNESS: Not Relevant
        ( D ) TOPOLOGY: both ( i i ) MOLECULE TYPE: protein ( x i ) SEQUENCE DESCRIPTION: SEQ ID NO:12:

```
Glu Leu Leu Gln Lys Tyr Val Thr Trp Asp Asp Lys
              5                      10
```